United States Patent [19]

Meyer et al.

[11] Patent Number: 4,693,741
[45] Date of Patent: Sep. 15, 1987

[54] N-PHENYLSULFONYL-N'-PYRIMIDINYLUREAS

[75] Inventors: Willy Meyer, Riehen; Werner Föry, Basel, both of Switzerland

[73] Assignee: Ciba-Geigy Corporation, Ardsley, N.Y.

[21] Appl. No.: 740,937

[22] Filed: Jun. 3, 1985

Related U.S. Application Data

[62] Division of Ser. No. 401,583, Jul. 26, 1982, Pat. No. 4,545,811.

[30] Foreign Application Priority Data

Aug. 6, 1981 [CH] Switzerland ............... 5075/81
Apr. 8, 1982 [CH] Switzerland ............... 2205/82

[51] Int. Cl.$^4$ ............... C07D 239/69; A01N 43/54
[52] U.S. Cl. ............... 71/92; 544/321
[58] Field of Search ............... 71/92; 544/321

[56] References Cited

FOREIGN PATENT DOCUMENTS 0009419 4/1980 European Pat. Off. .

*Primary Examiner*—John M. Ford

[57] ABSTRACT

N-Phenylsulfonyl-N'-pyrimidinyl- and -triazinylureas of the general formula

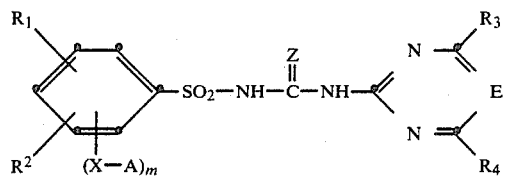

and the salts of these compounds with amines, alkali metal or alkaline earth metal bases or quaternary ammonium bases have good pre-emergence and post-emergence selective herbicidal properties and growth-regulating properties.

In this formula, A is a $C_1$–$C_6$-alkyl radical which is substituted by halogen, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-halogenoalkoxy, $C_1$–$C_4$-halogenoalkylthio, $C_1$–$C_4$-halogenoalkylsulfinyl or $C_1$–$C_4$-halogenoalkylsulfonyl, or is a $C_2$–$C_6$-alkenyl radical substituted by the above radicals, E is the methine group or nitrogen, X is oxygen, sulfur or a sulfinyl or sulfonyl bridge, Z is oxygen or sulfur, m is the number one or two, $R_1$ is hydrogen, halogen, $C_1$–$C_5$-alkyl, $C_2$–$C_5$-alkenyl or a —Y—$R_5$ radical, $R_2$ is hydrogen, halogen, $C_1$–$C_5$-alkyl, $C_2$–$C_5$-alkenyl, $C_1$–$C_4$-halogenoalkyl or a —Y—$R_5$, —COOR$_6$, —NO$_2$ or —CO—NR$_7$—R$_8$ radical, $R_3$ is hydrogen, $C_1$–$C_4$-alkyl, $C_1$–$C_4$-alkoxy, $C_1$–$C_4$-alkylthio, $C_1$–$C_4$-halogenoalkyl, halogen, $C_1$–$C_4$-halogenoalkoxy or alkoxyalkyl having not more than 4 carbon atoms, $R_4$ is $C_1$–$C_4$-halogenoalkoxy or $C_1$–$C_4$-halogenoalkylthio, $R_5$ and $R_6$ are each $C_1$–$C_5$-alkyl, $C_2$–$C_5$-alkenyl or $C_2$–$C_6$-alkynyl, $R_7$ and $R_8$ independently of one another are hydrogen, $C_1$–$C_5$-alkyl, $C_2$–$C_5$-alkenyl or $C_2$–$C_6$-alkynyl and Y is oxygen, sulfur or a sulfinyl or sulfonyl bridge, and A can also be an unsubstituted $C_2$–$C_6$-alkenyl radical if X is simultaneously oxygen.

24 Claims, No Drawings

N-PHENYLSULFONYL-N'-PYRIMIDINYLUREAS

This is a divisional of application Ser. No. 401,583 filed on July 26, 1982 now U.S. Pat. No. 4,545,811, dated Oct. 8, 1985.

The present invention relates to novel herbicidally active and plant growth-regulating N-phenylsulfonyl-N'-pyrimidinyl- and -triazinyl-ureas, processes for their preparation, compositions containing them as active substances, and their use for controlling weed, in particular for selectively controlling weeds in crops of useful plants or for regulating and inhibiting plant growth.

The N-phenylsulfonyl-N'-pyrimidinyl- and -triazinyl-ureas according to the invention are those of the general formula I

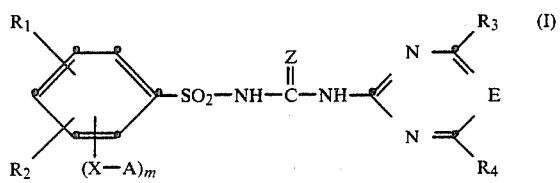

in which A is a $C_1$–$C_6$-alkyl radical which is substituted by halogen, $C_1$–$C_4$-alkoxy, $C_1$–$C_4$-alkylthio, $C_1$–$C_4$-alkylthio, $C_1$–$C_4$-alkylsulfinyl, $C_1$–$C_4$-alkylsulfonyl, $C_1$–$C_4$-halogenoalkoxy, $C_1$–$C_4$-halogenoalkylthio, $C_1$–$C_4$-halogenoalkylsulfinyl or $C_1$–$C_4$-halogenoalkylsulfonyl, or is a $C_2$–$C_6$-alkenyl radical substituted by the above radical, E is the methine group or nitrogen, X is oxygen, sulfur or a sulfinyl or sulfonyl bridge, Z is oxygen or sulfur, m is the number one or two, $R_1$ is hydrogen, halogen, $C_1$–$C_5$-alkyl, $C_2$–$C_5$-alkenyl or a —Y—$R_5$ radical, $R_2$ is hydrogen, halogen, $C_1$–$C_5$-alkyl, $C_2$–$C_5$-alkenyl, $C_1$–$C_4$-halogenoalkyl or a —Y—$R_5$, $COOR_6$, —$NO_2$ or —CO—$NR_7$—$R_8$ radical, $R_3$ is hydrogen, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, halogen or alkoxyalkyl having not more than 4 carbon atoms, $R_4$ is $C_1$–$C_4$-halogenoalkoxy or $C_1$–$C_4$-halogenoalkylthio, $R_5$ and $R_6$ are each $C_1$–$C_5$-alkyl, $C_2$–$C_5$-alkenyl or $C_2$–$C_6$-alkynyl, $R_7$ and $R_8$ independently of one another are hydrogen, $C_1$–$C_5$-alkyl, $C_2$–$C_5$-alkenyl or $C_2$–$C_6$-alkynyl and Y is oxygen, sulfur or a sulfinyl or sulfonyl bridge, and in which A can also be an unsubstituted $C_2$–$C_6$-alkenyl radical if X is simultaneously oxygen, and the salts of these compounds.

Urea compounds, triazine compounds and pyrimidine compounds having a herbicidal action are generally known. Arylsulfamoyl-heterocyclyl-aminocarbamoyl compounds having a herbicidal and plant growth regulating action have recently been disclosed, for example in Dutch Pat. No. 121,788, European Patent Publication Nos. 9,419 and 23,422, U.S. Pat. No. 4,127,405, German Offenlegungsschrift No. 2,715,786 and French Patent Specification No. 1,468,747.

In the definitions, alkyl is to be understood as meaning straight-chain or branched alkyl, for example methyl, ethyl, n-propyl, i-propyl, the four isomeric butyl radicals, n-amyl, i-amyl, 2-amyl, 3-amyl, n-hexyl and i-hexyl.

Alkoxy is to be understood as meaning methoxy, ethoxy, n-propoxy, i-propoxy and the four isomeric butoxy radicals, but especially methoxy, ethoxy or i-propoxy.

Examples of alkylthio are methylthio, ethylthio, n-propylthio, i-propylthio and n-butylthio, but especially methylthio and ethylthio.

Examples of alkenyl radicals are vinyl, allyl, isopropenyl, prop-1-enyl, but-1-enyl, but-2-enyl, but-3-enyl, isobut-1-enyl, isobut-2-enyl, pent-1-enyl, pent-2-enyl, pent-3-enyl and pent-4-enyl, but especially vinyl, allyl and pent-4-enyl.

Examples of alkylsulfinyl are methylsulfinyl, ethylsulfinyl, n-propylsulfinyl and n-butylsulfinyl, but especially methylsulfinyl and ethylsulfinyl.

Examples of alkylsulfonyl are methylsulfonyl, ethylsulfonyl, n-propylsulfonyl and n-butylsulfonyl, but especially methylsulfonyl and ethylsulfonyl.

Halogen in the definitions and in halogeno-alkyl, -alkoxy, -alkylsulfinyl, -alkylsulfonyl and -alkylthio is to be understood as meaning fluorine, chlorine or bromine, but preferably fluorine or chlorine.

Preferred halogenoalkyl radicals, which may also be constituents of larger substituent groups, for example of a halogenoalkoxy or halogenoalkylthio radical, are difluoromethyl, trifluoromethyl, perfluoroethyl, 2,2,2-trifluoroethyl, chlorofluoromethyl, bromofluoromethyl, 2-chloroethyl, 1,1,2,2-tetrafluoroethyl, 2-fluoroethyl, 2,2,2-trichloroethyl, bromodifluoromethyl, chlorodifluoromethyl, 1,1,2-trifluoro-2-chloroethyl, 1,1,2-trifluoro-2-bromoethyl and 1,1,2,3,3,3-hexafluoropropyl, but especially difluoromethyl, 2,2,2-trifluoroethyl and perfluoroethyl.

Alkynyl radicals in the definitions of the above symbols are as a rule propargyl, but-2-ynyl, but-3-ynyl and the isomeric pentynyl and hexynyl radicals, but the alkynyl radical is preferably propargyl or but-2- or -3-ynyl.

The invention also relates to the salts which the compounds of the formula I can form with amines, alkali metal and alkaline earth metal bases and quaternary ammonium bases.

Of the alkali metal and alkaline earth metal hydroxides, the hydroxides of lithium, sodium, potassium, magnesium and calcium, but especially those of sodium and potassium, are preferred salt-forming agents.

Examples of amines suitable for salt formation are primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, but especially ethylamine, propylamine, diethylamine and triethylamine, and in particular isopropylamine and diethanolamine.

Examples of quaternary ammonium bases are, in general, the cations of ammonium halide salts, for example the tetramethylammonium cation, the trimethylbenzylammonium cation, the triethylbenzylammonium cation, the tetraethylammonium cation, the trimethylethylammonium cation and the ammonium cation.

Preferred compounds of the formula I according to the invention are those in which (a) X or (b) Z is oxygen or (c) m is the number one and (d) the radicals $R_3$ and $R_4$ together contain not more than 4 carbon atoms.

Combination of the preferred features gives the following further preferred group of compounds of the formula I in which X and Z are oxygen, m is the number one and the radical —X—A occupies the ortho-position relative to the sulfonyl group.

Within this group, preferred compounds are moreover those in which the radicals $R_3$ and $R_4$ together contain not more than 4 carbon atoms.

Particularly preferred compounds within this subgroup are those in which $R_4$ is halogenoethoxy or halogenomethoxy. Of these, those in which $R_4$ is the 2,2,2-trifluoroethoxy radical or the difluoromethoxy radical are in turn preferred.

Specific preferred compounds are N-(2-difluoromethoxyphenyl-sulfonyl)-N'-[4-methoxy-6-(2,2,2-trifluoroethoxy)-1,3,5-triazin-2-yl]-urea, N-[2-(2-chloroethoxy)-phenylsulfonyl]-N'-[4-methoxy-6-(2,2,2-trifluoroethoxy)-1,3,5-triazin-2-yl]-urea, N-(2-trifluoromethoxyphenylsulfonyl)-N'-(4-difluoromethoxy-6-methyl-pyrimidin-2-yl)-urea and N-(2-difluoromethoxyphenylsulfonyl)-N'-(4-difluoromethoxy-6-methyl-pyrimidin-2-yl)-urea.

The compounds of the formula I are prepared in an inert organic solvent.

In a first process, the compounds of the formula I are obtained by a procedure which comprises reacting a phenylsulfonamide of the formula II

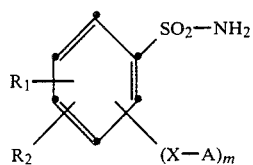 (II)

in which A, $R_1$, $R_2$, X and m are as defined under formula I, with an N-pyrimidinyl- or -triazinyl-carbamate of the formula III

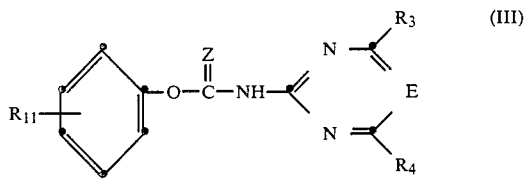 (III)

in which E, $R_3$, $R_4$ and Z are as defined under formula I and $R_{11}$ is hydrogen, halogen, nitro or $C_1$-$C_3$-alkyl, in the presence of a base.

In a second process, compounds of the formula I are obtained by a procedure which comprises reacting a phenylsulfonyl isocyanate or isothiocyanate of the formula IV

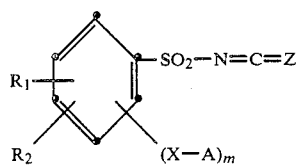 (IV)

in which A, $R_1$, $R_2$, m, X and Z are as defined under formula I, with an amine of the formula V

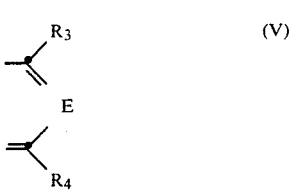 (V)

in which E, $R_3$ and $R_4$ are as defined under formula I, in the presence or absence of a base.

In a further process, the compounds of the formula I are prepared by a procedure which comprises reacting a sulfonamide of the formula II given above with an isocyanate or isothiocyanate of the formula VI

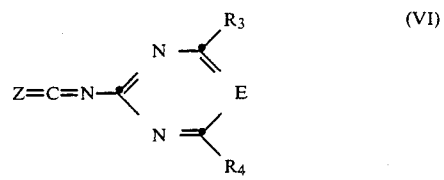 (VI)

in which E, $R_3$, $R_4$ and Z are as defined under formula I, in the presence or absence of a base.

Finally, the compounds of the formula I can also be obtained by a procedure which comprises reacting an N-phenylsulfonylcarbamate of the formula VII

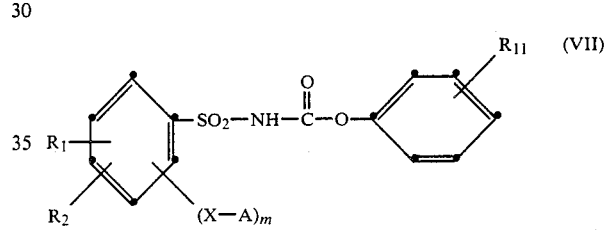 (VII)

in which A, $R_1$, $R_2$, m and X are as defined under formula I and $R_{11}$ is hydrogen, halogen, nitro or $C_1$-$C_3$-alkyl, with an amine of the formula V defined above.

If desired, the resulting ureas of the formula I can be converted into addition salts by means of amines, alkali metal or alkaline earth metal hydroxides or quaternary ammonium bases. This is effected, for example, by reaction with an equimolar amount of base and evaporation of the solvent.

The starting materials of the formulae II, IV and VII and the ortho-substituted hydroxyphenyl- or substituted ortho-hydroxyphenyl-sulfonamides of the formula VIII

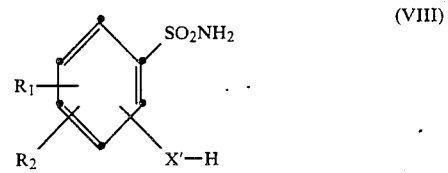 (VIII)

in which $R_1$ and $R_2$ are as defined under formula I and X' is oxygen or sulfur, as starting materials of certain sulfonamide representatives of the formula II, have been disclosed in European Patent Application No. 44,807.

Some of the starting materials of the formulae III, V and VI are known. Novel compounds of the formulae III and VI can be obtained by conventional methods from corresponding compounds of the formula V.

Novel fluoroalkoxy-amino-pyrimidines and -triazines of the formula V, their preparation and the preparation of corresponding compounds of the formulae III and VI therefrom have been disclosed in Swiss Patent Application No. 3527/82-8.

The reactions to give compounds of the formula I are advantageously carried out in aprotic, inert, organic, solvents, such as methylene chloride, tetrahydrofuran, acetonitrile, dioxane and toluene. Bases which can be used are inorganic bases, such as amines, for example triethylamine, quinuclidine, quinoline, pyridine and the like, and inorganic bases, such as hydrides, for example sodium hydride or calcium hydride, hydroxides, for example sodium hydroxide and potassium hydroxide, carbonates, for example sodium carbonate and potassium carbonate, and bicarbonates, for example potassium bicarbonate and sodium bicarbonate.

The reaction temperatures are preferably between $-20°$ and $+120°$ C. The reactions generally proceed slightly exothermically, and can be carried out at room temperature. For the purpose of shortening the reaction time or for initiating the reaction, the mixture is appropriately warmed to its boiling point for a short time.

The end products can be isolated by concentrating the mixture and/or evaporating off the solvent and can be purified by recrystallisation or trituration of the solid residue in solvents in which they are not readily soluble, such as ethers, aromatic hydrocarbons and chlorinated hydrocarbons.

The active substances of the formula I are stable compounds. Their handling requires no precautionary measures.

When used in relatively small amounts, the compounds of the formula I have good selectively growth-inhibiting and selectively herbicidal properties which make them excellent for use in crops of useful plants, in particular cereals, cotton, soybean, maize and rice. In some cases, weeds which have hitherto been affected only by total herbicides are also damaged.

The mode of action of these active substances is unusual. Many of them are translocatable, i.e they are taken up by the plant and transported to other points, where they then act. It is thus possible, for example, to damage perennial weeds as far as the roots by surface treatment. In contrast to other herbicides and growth regulators, the novel compounds of the formula I already act when applied in very small amounts.

The compounds of the formula I also have powerful plant growth regulating properties, which can result in an increase in the yield of crops or harvest. Moreover, many compounds of the formula I exhibit a concentration-dependent plant growth inhibiting action. The growth of both monocotyledons and dicotyledons is impaired.

Thus, for example, the growth of leguminosae frequently planted as cover crops in agriculture in tropical regions can be selectively inhibited by the compounds of the formula I, so that although soil erosion between crops is prevented, the cover crops cannot compete with the crop.

Inhibition of the vegetative growth enables many crop plants to be planted closer together, so that an increased yield in relation to soil area can be achieved.

A further mechanism of increasing yield with growth inhibitors is based on the fact that a greater amount of nutrients is available for flower and fruit formation, whilst vegetative growth is restricted.

The compounds of the formula I can also be used to prevent stored potatoes from sprouting. When potatoes are stored over winter, sprouts frequently develop, resulting in shrinkage, loss of weight and rotting.

When relatively large amounts are applied, the development of all the tested plants is damaged to the extent that the plants die.

The invention also relates to herbicidal and plant growth regulating compositions containing a novel active substance of the formula I, and to methods of pre-emergence and post-emergence control of weeds, of inhibiting the plant growth of monocotyledons and dicotyledons, especially grasses, tropical cover crops and tobacco side-shoots, and of regulating plant growth, especially of leguminosae.

The compounds of the formula I are used in unmodified form or, preferably, as compositions together with the assistants conventionally used in the art of formulation, and are therefore processed in a known manner to, for example, emulsion concentrates, solutions which can be sprayed directly or diluted, dilute emulsions, wettable powders, soluble powders, dusts, granules or compositions encapsulated in, for example, polymeric substances. The methods of application, such as spraying, misting, dusting, scattering or watering, like the type of composition, are chosen according to the intended aims and the given circumstances.

The formulations, i.e. the compositions, preparations or combinations containing the active substance of the formula I and, where relevant, a solid or liquid adjuvant are prepared in a known manner, for example by intimate mixing and/or grinding of the active substances with extenders, for example with solvents, solid carriers and, where appropriate, surface-active compounds (surfactants).

Suitable solvents include aromatic hydrocarbons, preferably $C_8$–$C_{12}$-fractions, for example xylene mixtures or substituted naphthalenes, phthalates, such as dibutyl phthalate or dioctyl phthalate, aliphatic hydrocarbons, such as cyclohexane or paraffins, alcohols and glycols and ethers and esters thereof, such as ethanol, ethylene glycol, ethylene glycol monomethyl ether or ethylene glycol monoethyl ether, ketones, such as cyclohexanone, highly polar solvents, such as N-methyl-2-pyrrolidone, dimethylsulfoxide or dimethylformamide, vegetable oils, which may be epoxidised, such as epoxidised coconut oil or soybean oil, and water.

Solid carriers used, for example for dusts and dispersible powders, are as a rule ground natural minerals, such as calcite, talc, kaolin, montmorillonite or attapulgite. Highly disperse silica or highly disperse absorbent polymers can also be added to improve the physical properties. Suitable granular, adsorbent carriers include porous materials, for example pumice, brick dust, sepiolite or bentonite, and examples of non-absorptive carriers include calcite and sand. In addition, a large number of pregranulated materials of inorganic or organic nature, such as, in particular, dolomite or comminuted plant residues, can be used.

Suitable surface-active compounds depend on the nature of the active substance of the formula I to be formulated and include non-ionic, cationic and/or anionic surfactants with good emulsifying, dispersing and wetting properties. Surfactants are also to be understood as meaning surfactant mixtures.

Suitable anionic surfactants can be either so-called water-soluble soaps or water-soluble synthetic surface-active compounds.

Soaps are the alkali metal, alkaline earth metal or substituted or unsubstituted ammonium salts of higher fatty acids ($C_{10}$–$C_{22}$), for example the Na or K salts of oleic acid or stearic acid, or of naturally occurring fatty acid mixtures, which can be isolated, for example, from coconut oil or tallow oil. Fatty acid methyl-taurine salts can also be used.

However, so-called synthetic surfactants are more frequently used, especially fatty sulfonates, fatty sulfates, sulfonated benzimidazole derivatives or alkylaryl sulfonates.

The fatty sulfonates and sulfates are as a rule in the form of alkali metal, alkaline earth metal or substituted or unsubstituted ammonium salts and contain an alkyl radical having 8 to 22 C atoms, alkyl also including the alkyl moiety of acyl radicals, for example the Na or Ca salt of lignin-sulfonic acid, of dodecyl-sulfuric acid ester or of a fatty alcohol sulfate mixture prepared from naturally occurring fatty acids. These also include the salts of sulfuric acid esters and sulfonic acids of fatty alcohol-/ethylene oxide adducts. The sulfonated benzimidazole derivatives preferably contain 2 sulfonic acid groups and a fatty acid radical having 8–22 C atoms. Examples of alkylaryl sulfonates are the Na, Ca or triethanolamine salts of dodecylbenzenesulfonic acid, dibutylnaphthalenesulfonic acid or a naphthalenesulfonic acid/formaldehyde condensate.

Corresponding phosphates, for example salts of the phosphoric acid ester of a p-nonylphenol/ethylene oxide 4:14 adduct, can also be used.

Suitable non-ionic surfactants include, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble adducts, containing 20 to 250 ethylene glycol ether groups and 10 to 100 propylene glycol ether groups, of polyethylene oxide and polypropylene glycol, ethylenediaminopolypropylene glycol and an alkylpolypropylene glycol having 1 to 10 carbon atoms in the alkyl chain. The above compounds usually contain 1 to 5 ethylene glycol units per propylene glycol unit.

Examples of non-ionic surfactants include nonylphenol-polyethoxyethanols, castor oil polyglycol ethers, polypropylene/polyethylene oxide adducts, tributylphenoxypolyethanol, polyethylene glycol and octylphenoxypolyethoxyethanol.

Fatty acid esters of polyoxyethylene sorbitan, such as polyoxyethylene sorbitan trioleate, can also be used.

The cationic surfactants are, in particular, quaternary ammonium salts which contain at least one alkyl radical having 8 to 22 C atoms as an N-substituent and, as further substituents, lower alkyl radicals, which may be halogenated, benzyl or lower hydroxyalky radicals. The salts are preferably in the form of halides, methylsulfates or ethylsulfates, for example stearyltrimethylammonium chloride and benzyldi-(2-chloroethyl)-ethylammonium bromide.

The surfactants customary in the art of formulation are described in, inter alia, the following publications: "McCutcheon's Detergents and Emulsifiers Annual" MC Publishing Corp., Ridgewood, N.J., 1979 and Sisley and Wood, "Encyclopedia of Surface Active Agents". Chemical Publishing Co., Inc. New York, 1964.

The pesticidal preparations as a rule contain 0.1 to 95%, in particular 0.1 to 80%, of active substance of the formula I, 1 to 99.9% of a solid or liquid adjuvant and 0 to 25%, in particular 0.1 to 25%, of a surfactant.

In particular, preferred formulations have the following compositions: (%=percent by weight)

| Emulsifiable concentrates | |
|---|---|
| Active substance: | 1 to 20%, preferably 5 to 10% |
| Surfactant: | 5 to 30%, preferably 10 to 20% |
| Liquid carrier: | 50 to 94%, preferably 70 to 85%. |
| Dusts | |
| Active substance: | 0.1 to 10%, preferably 0.1 to 1% |
| Solid carrier: | 99.9 to 90%, preferably 99.9 to 99%. |
| Suspension concentrates | |
| Active substance: | 5 to 75%, preferably 10 to 50% |
| Water: | 94 to 25%, preferably 90 to 30% |
| Surfactant: | 1 to 40%, preferably 2 to 30%. |
| Wettable powders | |
| Active substance: | 0.5 to 90%, preferably 1 to 80% |
| Surfactant: | 0.5 to 20%, preferably 1 to 15% |
| Solid carrier: | 5 to 95%, preferably 15 to 90%. |
| Granules | |
| Active substance: | 0.5 to 30%, preferably 3 to 15% |
| Solid carrier: | 99.5 to 70%, preferably 97 to 85%. |

Whilst concentrated compositions are preferred as commercial products, the end consumer as a rule uses dilute compositions. The use forms can be diluted down to 0.001% of active substance. The amounts applied are as a rule 0.01 to 10 kg of active substance/ha, preferably 0.025 to 5 kg of active substance/ha.

The compositions can also contain other additives such as stabilisers, antifoams, viscosity regulators, binders, tackifiers and fertilisers or other active substances to achieve special effects.

In the following examples, the temperatures are given in degrees centigrade °C. and the pressures are given in millibars mb.

PREPARATION EXAMPLES

Example 1

N-(2-Difluoromethoxyphenyl-sulfonyl)-N'-[4-methoxy-6-(2,2,2-trifluoroethoxy)-1,3,5-triazin-2-yl]-urea (a) 124.6 g of 2-difluoromethoxyphenyl-sulfonyl isocyanate in 100 ml of dioxane are added dropwise to a suspension of 80.3 g of 2-amino-4-chloro-6-methoxy-1,3,5-triazine in 400 ml of absolute dioxane in the course of 10 minutes. The reaction mixture is warmed to 90°–100° for 3 hours, and the solution is then cooled and concentrated to give 180 g of N-(2-difluoromethoxyphenyl-sulfonyl)-N'-(4-chloro-6-methoxy-1,3,5-triazin-2-yl)-urea of melting point 167°–168°.

(b) A mixture of 8.2 g of N-(2-difluoromethoxyphenyl-sulfonyl)-N'-(4-chloro-6-methoxy-1,3,5-triazin-2-yl)-urea, 60 ml of dioxane, 20 ml of 2,2,2-trifluoroethanol and 5.5 g of potassium carbonate is stirred at 55°–60° for 12 hours and then taken up in 300 ml of water and filtered over active charcoal. After the mixture has been acidified with 2N hydrochloric acid, the product precipitates and is separated off by filtration. Yield: 7.7 g of N-(2-difluoromethoxyphenyl-sulfonyl)-N'-[4-methoxy-6-(2,2,2-trifluoroethoxy)-1,3,5-triazin-2-yl]-urea of melting point 155°–157°.

Example 2

N-(2-Difluoromethoxyphenyl-sulfonyl)-N'-(4-difluoromethoxy-6-methyl-pyrimidin-2-yl)-urea (a) Gaseous difluorochloromethane is passed into a solution of 62.5 g of 2-amino-4-hydroxy-6-methyl-pyrimidine in 500 ml of water, 100 ml of 40% sodium hydroxide solution and 100 ml of dioxane at a temperature of 70°–75° C. over a period of 12 hours. During this period, at hourly intervals, a total of 160 g of solid sodium hydroxide is added in equal portions. The organic phase is separated off and concentrated to about 1/10 of its volume, the residue is poured into water and the solid which has precipitated is separated off to give 39.9 g of 2-amino-4-difluoromethoxy-6-methyl-pyrimidine of melting point 136°–137° C.

(b) A mixture of 2.5 g of 2-difluoromethoxyphenyl-sulfonyl isocyanate, 1.75 g of 2-amino-4-difluoromethoxy-6-methyl-pyrimidine and 30 ml of absolute dioxane is stirred at a temperature of 70°–75° C. for 2 hours. The solution is evaporated and the residue is crystallised from ether to give 4.0 g of N-(2-difluoromethoxyphenyl-sulfonyl)-N'-(4-difluoromethoxy-6-methyl-pyrimidin-2-yl)-urea of melting point 163°–164° C.

Example 3

N-[2-(2-Ethoxy-ethoxy)-phenyl-sulfonyl]-N'-(4-difluoromethoxy-6-methyl-pyrimidin-2-yl)-urea (a) 3.9 g (0.025 mol) of phenyl chloroformate and 0.05 g of 4-dimethylamino-pyridine are added in succession to a solution of 9.0 g (0.05 mol) of 2-amino-4-difluoromethoxy-6-methyl-pyrimidine in 30 ml of absolute tetrahydrofuran. The solution is stirred at 20°–25° C. for 24 hours and the reaction mixture is then diluted with 250 ml of ethyl acetate and the precipitate is separated off. 3.1 g of 2-amino-4-difluoromethoxy-6-methyl-pyrimidine hydrochloride of melting point 204°–205° C. (decomposition) are thus obtained. To remove the residual starting material, the filtrate is eluted over a column containing the ion exchanger I ® (MERCK), and the eluate is dried over sodium sulfate and evaporated. 4.0 g of 2-phenoxycarbonylamino-4-difluoromethoxy-6-methyl-pyrimidine are obtained as the crude product in the form of a viscous oil. After crystallisation, the product has a melting point of 56°–58° C.

$^1$H—NMR (CDCl$_3$): δ=2.5 (s, CH$_3$), 6.45 (s, 1H), 7.0–7.5 (5H), 7.56 (t, J=70 Hz, CHF$_2$) and 9.0 (NH) ppm.

(b) 1.8 g (0.012 mol) of 1,5-diazabicyclo(5.4.0)undec-5-ene are added to a solution of 3.5 g (0.012 mol) of 2-phenoxycarbonylamino-4-difluoromethoxy-6-methyl-pyrimidine, in the form of the crude product, and 2.9 g (0.012 mol) of 2-(2-ethoxy-ethoxy)-benzenesulfonamide in 100 ml of absolute acetonitrile and the mixture is stirred at 20°–25° C. for 1 hour and then diluted with 500 ml of water and acidified with hydrochloric acid. The oil which separates out is taken up in 200 ml of ethyl acetate and the mixture is dried over sodium sulfate and evaporated. The oily residue is crystallised from diethyl ether and acetone to give N-[2-(2-ethoxy-ethoxy)-phenyl-sulfonyl]-N'-(4-difluoromethoxy-6-methyl-pyrimidin-2-yl)-urea of melting point 90°–95° C. (decomposition) as colourless crystals in a yield of 2.7 g.

Example 4

2-Amino-4-difluoromethylthio-6-methoxy-1,3,5-triazine 10.0 g of gaseous difluorochloromethane are passed into a suspension of 5.0 g of 2-amino-4-mercapto-6-methoxy-1,3,5-triazine and 4.8 g of potassium carbonate in 100 ml of dimethylformamide at a temperature of 70°–75° C. over a period of 90 minutes. The reaction mixture is evaporated, the residue is stirred with water and the solid precipitate is separated off to give 1.6 g of 2-amino-4-difluoromethylthio-6-methoxy-1,3,5-triazine of melting point 146°–150° C.

Example 5

2-Amino-4-chloro-6-difluoromethoxy-primidine

A suspension of 16.4 g of 2-amino-4,6-dichloropyrimidine in 100 ml of 40% sodium hydroxide solution is stirred at a temperature of 95°–100° C. for 1 hour. 200 ml of dioxane are added, and 20 g of gaseous difluorochloromethane are passed in at a temperature of 70°–75° C. in the course of 1 hour. The organic phase is separated off and concentrated to about 1/5 of its volume, the residue is poured into water and the solid precipitate is separated off to give 6 g of 2-amino-4-chloro-6-difluoromethoxy-pyrimidine of melting point 118°–119° C.

Example 6

2-Amino-4-difluoromethoxy-6-methoxy-pyrimidine 19.2 g of 2-amino-4,6-dimethoxy-pyrimidine hydrochloride are heated at 150° C. for 2 hours, during which methyl chloride is detached to give 2-amino-4-hydroxy-6-methoxy-pyrimidine. 80 ml of 40% sodium hydroxide solution and 100 ml of dioxane are added, and 22 g of difluorochloromethane are passed in at 70°–75° in the course of ¾ of an hour. The organic phase is separated off and concentrated to about 1/5 of its volume, the residue is poured into water and the solid precipitate is separated off to give 2.4 g of 2-amino-4-difluoromethoxy-6-methoxy-pyrimidine of melting point 106°–107° C.

Example 7

2-Amino-4-methyl-6-[1,1,2-trifluoro-2-chloroethoxy]-pyrimidine 25 g of 2-amino-4-hydroxy-6-methyl-pyrimidine, 25.6 g of chlorotrifluoroethylene, 13.8 of potassium hydroxide and 200 ml of dimethylformamide are stirred together at 60° in an autoclave for 8 hours. The mixture is diluted with water and extracted with ethyl acetate and the extract is evaporated to give a dark oil. A little methylene chloride is added and the crystalline precipitate formed is separated off to give 8.7 g of 2-amino-4-methyl-6-(1,1,2,-trifluoro-2-chloro-ethoxy)-pyrimidine of melting point 73°–74° C.

The end products listed in the following table are obtained in a similar manner.

TABLE 1

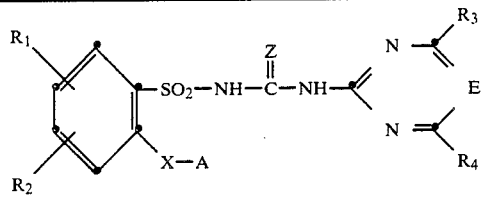

| No. | R₁ | R₂ | X | A | Z | E | R₃ | R₄ | Melting point [°C.] |
|---|---|---|---|---|---|---|---|---|---|
| 1 | H | H | O | CHF₂ | O | N | CH₃ | —O—CH₂—CF₃ | 110–112° |
| 2 | H | H | O | CHF₂ | O | N | C₂H₅ | —O—CH₂—CF₃ | 129–131° |
| 3 | H | H | O | CHF₂ | O | N | OC₂H₅ | —O—CH₂—CF₃ | 147–148° |
| 4 | H | H | O | CHF₂ | S | N | OCH₃ | —O—CH₂—CF₃ | |
| 5 | H | H | S | CHF₂ | O | N | OCH₃ | —O—CH₂—CF₃ | 152–154° |
| 6 | H | H | O | CHF₂ | O | N | OCH₃ | —O—CH₂—CF₃ | 155–157° |
| 7 | H | H | O | —CF₂—CHF₂ | O | N | OCH₃ | —O—CH₂—CF₃ | 169–170° |
| 8 | H | H | O | CF₃ | O | N | OCH₃ | —O—CH₂—CF₃ | 157–159° |
| 9 | H | H | O | CHF₂ | O | CH | OCH₃ | —O—CH₂—CF₃ | 164–165° |
| 10 | H | H | O | CHF₂ | O | CH | CH₃ | —O—CH₂—CF₃ | 157–158° |
| 11 | H | H | O | CHF₂ | O | CH | Cl | —O—CH₂—CF₃ | 147–148° |
| 12 | H | H | O | CHF₂ | O | CH | SCH₃ | —O—CH₂—CF₃ | |
| 13 | H | H | O | CHF₂ | O | CH | CH₂Cl | —O—CH₂—CF₃ | 114–118° |
| 14 | H | H | S | CHF₂ | O | CH | OCH₃ | —O—CH₂—CF₃ | 169–170° |
| 15 | H | H | O | CHF₂ | O | N | OCH₃ | —O—CH₂—CJH₂Cl | 119–120° |
| 16 | H | H | O | CHF₂ | O | N | OCH₃ | —O—CH₂—CH₂F | 94–95° |
| 17 | H | H | O | CHF₂ | O | N | OCH₃ | —O—CH₂—CH₂Br | |
| 18 | H | H | O | CHF₂ | O | CH | OCH₃ | —O—CH₂—CH₂Cl | |
| 19 | H | H | O | CHF₂ | O | CH | OCH₃ | —O—CH₂—CH₂F | 88° (decomposition) |
| 20 | 5-F | H | O | CHF₂ | O | N | OCH₃ | —O—CH₂—CF₃ | 117–119° |
| 21 | H | 6-Cl | O | CHF₂ | O | N | OCH₃ | —O—CH₂—CF₃ | 126–127° |
| 22 | 5-F | H | O | CHF₂ | O | CH | OCH₃ | —O—CH₂—CF₃ | |
| 23 | 5-F | H | O | CHF₂ | O | CH | OCH₃ | —O—CH₂—CH₂Cl | 141–148° |
| 24 | H | H | O | —CH₂—CH=CH₂ | O | N | OCH₃ | —O—CH₂—CF₃ | |
| 25 | H | H | O | —CH₂—CH₂Cl | O | N | OCH₃ | —O—CH₂—CF₃ | 135–137° |
| 26 | H | H | O | —CCl=CHCl | O | N | OCH₃ | —O—CH₂—CF₃ | 133–134° |
| 27 | H | H | O | —CH₂—CH₂—OCH₃ | O | N | OCH₃ | —O—CH₂—CF₃ | |
| 28 | H | H | O | —CH₂—OCH₃ | O | N | OCH₃ | —O—CH₂—CF₃ | |
| 29 | 5-Cl | H | O | —CH₂—CH=CH₂ | O | N | OCH₃ | —O—CH₂—CF₃ | |
| 30 | 5-F | H | O | —CH₂—CH=CH₂ | O | N | OCH₃ | —O—CH₂—CF₃ | |
| 31 | H | H | O | CHF₂ | O | CH | CH₃ | —O—CHF₂ | 161–162° |
| 32 | H | H | O | CHF₂ | O | CH | CF₃ | OCHF₂ | 130–131° |
| 33 | H | H | O | CHF₂ | O | CH | OCH₃ | OCHF₂ | 168–169° |
| 34 | H | H | O | CHF₂ | O | CH | Cl | OCHF₂ | 133–134° |
| 35 | H | H | O | CHF₂ | O | CH | C₂H₅ | OCHF₂ | 145–146° |
| 36 | H | H | O | CHF₂ | O | CH | SCH₃ | OCHF₂ | |
| 37 | H | H | O | CHF₂ | O | CH | CH₂F | OCHF₂ | |
| 38 | H | H | O | CHF₂ | O | CH | CH₃ | SCHF₂ | |
| 39 | H | H | O | CHF₂ | O | N | OCH₃ | SCHF₂ | 127–129° |
| 40 | H | H | O | CHF₂ | O | N | OCH₃ | OCHF₂ | |
| 41 | H | H | O | CHF₂ | O | N | —O—CH₂—CF₃ | —O—CH₂—CF₃ | |
| 42 | H | H | O | CHF₂ | O | N | OCH₃ | —O—CH₂—CHCl₂ | |
| 43 | H | H | O | CHF₂ | O | N | OCH₃ | —O—CH₂—CHCl—CH₂Cl | |
| 44 | H | H | O | CHF₂ | O | N | Cl | —O—CH₂—CF₃ | |
| 45 | H | H | O | CHF₂ | O | CH | —O—CH₂—CF₃ | OCHF₂ | |
| 46 | H | H | O | —CH₂—OCH₃ | O | CH | CH₃ | OCHF₂ | |
| 47 | H | H | O | —CH₂—OCH₃ | O | CH | CF₃ | OCHF₂ | |
| 48 | H | H | O | —CH₂—OCH₃ | O | CH | Cl | OCHF₂ | |
| 49 | H | H | O | —CH₂—OCH₃ | O | CH | OCH₃ | OCHF₂ | |
| 50 | H | H | O | —CH₂—OCH₃ | O | CH | C₂H₅ | OCHF₂ | |
| 51 | H | H | O | —CH₂—OCH₃ | O | CH | CH₂F | OCHF₂ | |
| 52 | H | H | O | —CH₂—OCH₃ | O | CH | SCH₃ | OCHF₂ | |
| 53 | H | H | O | —CH₂—OCH₃ | O | CH | OCH₃ | SCHF₂ | |
| 54 | H | H | O | —CH₂—OCH₃ | O | N | CH₃ | OCHF₂ | |
| 55 | H | H | O | —CH₂—OCH₃ | O | N | OCH₃ | —O—CH₂—CH₂Cl | |
| 56 | H | H | O | —CH₂—OCH₃ | O | N | OCH₃ | —O—CH₂—CH₂F | |
| 57 | H | H | O | —CH₂—OCH₃ | O | N | OCH₃ | —O—CH₂—CHCl₂ | |
| 58 | H | H | O | —CH₂—OCH₃ | O | N | OCH₃ | —O—CH₂—CHCl—CH₂Cl | |
| 59 | H | H | O | —CH₂—OCH₃ | O | N | CH₃ | —O—CH₂—CF₃ | |
| 60 | H | H | O | —CH₂—OCH₃ | O | CH | CH₃ | —O—CH₂—CF₃ | |
| 61 | H | H | O | —CH₂—OCH₃ | O | CH | Cl | —O—CH₂—CF₃ | |
| 62 | H | H | O | —CH₂—OCH₃ | O | CH | OCH₃ | —O—CH₂—CF₃ | |
| 63 | H | H | O | —CH₂—CH=CH₂ | O | CH | CH₃ | OCHF₂ | 180–184° |
| 64 | H | H | O | —CH₂—CH=CH₂ | O | CH | CF₃ | OCHF₂ | |
| 65 | H | H | O | —CH₂—CH=CH₂ | O | CH | Cl | OCHF₂ | |
| 66 | H | H | O | —CH₂—CH=CH₂ | O | CH | OCH₃ | OCHF₂ | |
| 67 | H | H | O | —CH₂—CH=CH₂ | O | CH | C₂H₅ | OCHF₂ | |

TABLE 1-continued $$\text{R}_1\text{-}\underset{\text{R}_2}{\text{C}_6\text{H}_3}\text{(X-A)-SO}_2\text{-NH-}\underset{\|Z}{\text{C}}\text{-NH-C(=N-CR}_3\text{=E-CR}_4\text{=N-)}$$

| No. | R₁ | R₂ | X | A | Z | E | R₃ | R₄ | Melting point [°C.] |
|---|---|---|---|---|---|---|---|---|---|
| 68 | H | H | O | —CH₂—CH=CH₂ | O | CH | CH₂F | OCHF₂ | |
| 69 | H | H | O | —CH₂—CH=CH₂ | O | CH | SCH₃ | OCHF₂ | |
| 70 | H | H | O | —CH₂—CH=CH₂ | O | CH | OCH₃ | SCHF₂ | |
| 71 | H | H | O | —CH₂—CH=CH₂ | O | N | CH₃ | OCHF₂ | |
| 72 | H | H | O | —CH₂—CH=CH₂ | O | N | OCH₃ | —O—CH₂—CH₂Cl | |
| 73 | H | H | O | —CH₂—CH=CH₂ | O | N | OCH₃ | —O—CH₂—CH₂F | |
| 74 | H | H | O | —CH₂—CH=CH₂ | O | N | OCH₃ | —O—CH₂—CHCl₂ | |
| 75 | H | H | O | —CH₂—CH=CH₂ | O | N | OCH₃ | —O—CH₂—CHCl—CH₂Cl | |
| 76 | H | H | O | —CH₂—CH=CH₂ | O | N | CH₃ | —O—CH₂—CF₃ | |
| 77 | H | H | O | —CH₂—CH=CH₂ | O | CH | CH₃ | —O—CH₂—CF₃ | |
| 78 | H | H | O | —CH₂—CH=CH₂ | O | CH | Cl | —O—CH₂—CF₃ | |
| 79 | H | H | O | —CH₂—CH=CH₂ | O | CH | OCH₃ | —O—CH₂—CF₃ | 190–200° |
| 80 | H | H | O | —CF₂—CF₃ | O | CH | CH₃ | OCHF₂ | 185–186° |
| 81 | H | H | O | —CF₂—CF₃ | O | CH | CF₃ | OCHF₂ | |
| 82 | H | H | O | —CF₂—CF₃ | O | CH | Cl | OCHF₂ | |
| 83 | H | H | O | —CF₂—CF₃ | O | CH | OCH₃ | OCHF₂ | |
| 84 | H | H | O | —CF₂—CF₃ | O | CH | C₂H₅ | OCHF₂ | |
| 85 | H | H | O | —CF₂—CF₃ | O | CH | CH₂F | OCHF₂ | |
| 86 | H | H | O | —CF₂—CF₃ | O | CH | SCH₃ | OCHF₂ | |
| 87 | H | H | O | —CF₂—CF₃ | O | CH | OCH₃ | SCHF₂ | |
| 88 | H | H | O | —CF₂—CF₃ | O | N | CH₃ | OCHF₂ | |
| 89 | H | H | O | —CF₂—CF₃ | O | N | OCH₃ | —O—CH₂—CH₂Cl | |
| 90 | H | H | O | —CF₂—CF₃ | O | N | OCH₃ | —O—CH₂—CH₂F | |
| 91 | H | H | O | —CF₂—CF₃ | O | N | OCH₃ | —O—CH₂—CHCl₂ | |
| 92 | H | H | O | —CF₂—CF₃ | O | N | OCH₃ | —O—CH₂—CHCl—CH₂Cl | |
| 93 | H | H | O | —CF₂—CF₃ | O | N | CH₃ | —O—CH₂CF₃ | |
| 94 | H | H | O | —CF₂—CF₃ | O | CH | CH₃ | —O—CH₂CF₃ | |
| 95 | H | H | O | —CF₂—CF₃ | O | CH | Cl | —O—CH₂—CF₃ | |
| 96 | H | H | O | —CF₂—CF₃ | O | CH | OCH₃ | —O—CH₂—CF₃ | 166–167° |
| 97 | H | H | O | —CF₂—CF₃ | O | N | OCH₃ | —O—CH₂—CF₃ | 182–183° |
| 98 | H | H | O | —CH₂—CH₂—OCH₃ | O | CH | CH₃ | OCHF₂ | 148–149° |
| 99 | H | H | O | —CH₂—CH₂—OCH₃ | O | CH | CF₃ | OCHF₂ | |
| 100 | H | H | O | —CH₂—CH₂—OCH₃ | O | CH | Cl | OCHF₂ | 142–143° |
| 101 | H | H | O | —CH₂—CH₂—OCH₃ | O | CH | OCH₃ | OCHF₂ | 157–158° |
| 102 | H | H | O | —CH₂—CH₂—OCH₃ | O | CH | C₂F₅ | OCHF₂ | |
| 103 | H | H | O | —CH₂—CH₂—OCH₃ | O | CH | CH₂F | OCHF₂ | |
| 104 | H | H | O | —CH₂—CH₂—OCH₃ | O | CH | SCH₃ | OCHF₂ | |
| 105 | H | H | O | —CH₂—CH₂—OCH₃ | O | CH | OCH₃ | SCHF₂ | |
| 106 | H | H | O | —CH₂—CH₂—OCH₃ | O | N | CH₃ | OCHF₂ | |
| 107 | H | H | O | —CH₂—CH₂—OCH₃ | O | N | OCH₃ | —O—CH₂—CH₂Cl | |
| 108 | H | H | O | —CH₂—CH₂—OCH₃ | O | N | OCH₃ | —O—CH₂—CH₂F | |
| 109 | H | H | O | —CH₂—CH₂—OCH₃ | O | N | OCH₃ | —O—CH₂—CHCl₂ | |
| 110 | H | H | O | —CH₂—CH₂—OCH₃ | O | N | OCH₃ | —O—CH₂—CHCl—CH₂Cl | |
| 111 | H | H | O | —CH₂—CH₂—OCH₃ | O | N | CH₃ | —O—CH₂—CF₃ | |
| 112 | H | H | O | —CH₂—CH₂—OCH₃ | O | CH | CH₃ | —O—CH₂—CF₃ | |
| 113 | H | H | O | —CH₂—CH₂—OCH₃ | O | CH | Cl | —O—CH₂—CF₃ | |
| 114 | H | H | O | —CH₂—CH₂—OCH₃ | O | CH | OCH₃ | —O—CH₂—CF₃ | |
| 115 | H | H | O | —CH₂—CH₂Cl | O | CH | CH₃ | OCHF₂ | 182–183° |
| 116 | H | H | O | —CH₂—CH₂Cl | O | CH | CF₃ | OCHF₂ | |
| 117 | H | H | O | —CH₂—CH₂Cl | O | CH | Cl | OCHF₂ | |
| 118 | H | H | O | —CH₂—CH₂Cl | O | CH | OCH₃ | OCHF₂ | |
| 119 | H | H | O | —CH₂—CH₂Cl | O | CH | C₂H₅ | OCHF₂ | |
| 120 | H | H | O | —CH₂—CH₂Cl | O | CH | CH₂F | OCHF₂ | |
| 121 | H | H | O | —CH₂—CH₂Cl | O | CH | SCH₃ | OCHF₂ | |
| 122 | H | H | O | —CH₂—CH₂Cl | O | CH | OCH₃ | SCHF₂ | |
| 123 | H | H | O | —CH₂—CH₂Cl | O | N | CH₃ | OCHF₂ | |
| 124 | H | H | O | —CH₂—CH₂Cl | O | N | OCH₃ | —O—CH₂—CH₂Cl | |
| 125 | H | H | O | —CH₂—CH₂Cl | O | N | OCH₃ | —O—CH₂—CH₂F | |
| 126 | H | H | O | —CH₂—CH₂Cl | O | N | OCH₃ | —O—CH₂—CHCl₂ | |
| 127 | H | H | O | —CH₂—CH₂Cl | O | N | OCH₃ | —O—CH₂—CHCl—CH₂Cl | |
| 128 | H | H | O | —CH₂—CH₂Cl | O | N | CH₃ | —O—CH₂—CF₃ | |
| 129 | H | H | O | —CH₂—CH₂Cl | O | CH | CH₃ | —O—CH₂—CF₃ | |
| 130 | H | H | O | —CH₂—CH₂Cl | O | CH | Cl | —O—CH₂—CF₃ | |
| 131 | H | H | O | —CH₂—CH₂Cl | O | CH | OCH₃ | —O—CH₂—CF₃ | |
| 132 | H | H | O | —CCl=CHCl | O | CH | CH₃ | OCHF₂ | 216–217° (decomposition) |
| 133 | H | H | O | —CCl=CHCl | O | CH | CF₃ | OCHF₂ | |
| 134 | H | H | O | —CCl=CHCl | O | CH | Cl | OCHF₂ | 195–196° |

TABLE 1-continued

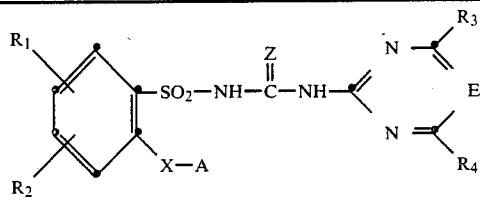

| No. | R₁ | R₂ | X | A | Z | E | R₃ | R₄ | Melting point [°C.] |
|---|---|---|---|---|---|---|---|---|---|
| 135 | H | H | O | —CCl=CHCl | O | CH | OCH₃ | OCHF₂ | |
| 136 | H | H | O | —CCl=CHCl | O | CH | C₂H₅ | OCHF₂ | |
| 137 | H | H | O | —CCl=CHCl | O | CH | CH₂F | OCHF₂ | |
| 138 | H | H | O | —CCl=CHCl | O | CH | SCH₃ | OCHF₂ | |
| 139 | H | H | O | —CCl=CHCl | O | CH | OCH₃ | SCHF₂ | |
| 140 | H | H | O | —CCl=CHCl | O | N | CH₃ | OCHF₂ | |
| 141 | H | H | O | —CCl=CHCl | O | N | OCH₃ | —O—CH₂—CH₂Cl | |
| 142 | H | H | O | —CCl=CHCl | O | N | OCH₃ | —O—CH₂—CH₂F | |
| 143 | H | H | O | —CCl=CHCl | O | N | OCH₃ | —O—CH₂—CHCl₂ | |
| 144 | H | H | O | —CCl=CHCl | O | N | OCH₃ | —O—CH₂—CHCl—CH₂Cl | |
| 145 | H | H | O | —CCl=CHCl | O | N | CH₃ | —O—CH₂—CF₃ | |
| 146 | H | H | O | —CCl=CHCl | O | CH | CH₃ | —O—CH₂—CF₃ | |
| 147 | H | H | O | —CCl=CHCl | O | CH | Cl | —O—CH₂—CF₃ | |
| 148 | H | H | O | —CCl=CHCl | O | CH | OCH₃ | —O—CH₂—CF₃ | 193–194° |
| 149 | H | H | O | —CH₂—CF₃ | O | CH | CH₃ | OCHF₂ | |
| 150 | H | H | O | —CH₂—CF₃ | O | CH | CF₃ | OCHF₂ | |
| 151 | H | H | O | —CH₂—CF₃ | O | CH | Cl | OCHF₂ | |
| 152 | H | H | O | —CH₂—CF₃ | O | CH | OCH₃ | OCHF₂ | |
| 153 | H | H | O | —CH₂—CF₃ | O | CH | C₂H₅ | OCHF₂ | |
| 154 | H | H | O | —CH₂—CF₃ | O | CH | CH₂F | OCHF₂ | |
| 155 | H | H | O | —CH₂—CF₃ | O | CH | SCH₃ | OCHF₂ | |
| 156 | H | H | O | —CH₂—CF₃ | O | CH | OCH₃ | SCHF₂ | |
| 157 | H | H | O | —CH₂—CF₃ | O | N | CH₃ | OCHF₂ | |
| 158 | H | H | O | —CH₂—CF₃ | O | N | OCH₃ | —O—CH₂—CH₂Cl | |
| 159 | H | H | O | —CH₂—CF₃ | O | N | OCH₃ | —O—CH₂—CH₂F | |
| 160 | H | H | O | —CH₂—CF₃ | O | N | OCH₃ | —O—CH₂—CHCl₂ | |
| 161 | H | H | O | —CH₂—CF₃ | O | N | OCH₃ | —O—CH₂—CHCl—CH₂Cl | |
| 162 | H | H | O | —CH₂—CF₃ | O | N | CH₃ | —O—CH₂—CF₃ | |
| 163 | H | H | O | —CH₂—CF₃ | O | CH | CH₃ | —O—CH₂—CF₃ | |
| 164 | H | H | O | —CH₂—CF₃ | O | CH | Cl | —O—CH₂—CF₃ | |
| 165 | H | H | O | —CH₂—CF₃ | O | CH | OCH₃ | —O—CH₂—CF₃ | |
| 166 | H | H | O | —CH₂—CF₃ | O | N | OCH₃ | —O—CH₂—CF₃ | |
| 167 | H | H | O | —CF₂—CHF₂ | O | CH | CH₃ | OCHF₂ | 174–175° |
| 168 | H | H | O | —CF₂—CHF₂ | O | CH | CF₃ | OCHF₂ | |
| 169 | H | H | O | —CF₂—CHF₂ | O | CH | Cl | OCHF₂ | |
| 170 | H | H | O | —CF₂—CHF₂ | O | CH | OCH₃ | OCHF₂ | |
| 171 | H | H | O | —CF₂—CHF₂ | O | CH | C₂H₅ | OCHF₂ | |
| 172 | H | H | O | —CF₂—CHF₂ | O | CH | CH₂F | OCHF₂ | |
| 173 | H | H | O | —CF₂—CHF₂ | O | CH | SCH₃ | OCHF₂ | |
| 174 | H | H | O | —CF₂—CHF₂ | O | CH | OCH₃ | SCHF₂ | |
| 175 | H | H | O | —CF₂—CHF₂ | O | N | CH₃ | OCHF₂ | |
| 176 | H | H | O | —CF₂—CHF₂ | O | N | OCH₃ | —O—CH₂—CH₂Cl | |
| 177 | H | H | O | —CF₂—CHF₂ | O | N | OCH₃ | —O—CH₂—CH₂F | |
| 178 | H | H | O | —CF₂—CHF₂ | O | N | OCH₃ | —O—CH₂—CHCl₂ | |
| 179 | H | H | O | —CF₂—CHF₂ | O | N | OCH₃ | —O—CH₂—CHCl—CH₂Cl | |
| 180 | H | H | O | —CF₂—CHF₂ | O | N | CH₃ | —O—CH₂—CF₃ | |
| 181 | H | H | O | —CF₂—CHF₂ | O | CH | CH₃ | —O—CH₂—CF₃ | |
| 182 | H | H | O | —CF₂—CHF₂ | O | CH | Cl | —O—CH₂—CF₃ | |
| 183 | H | H | O | —CF₂—CHF₂ | O | CH | OCH₃ | —O—CH₂—CF₃ | |
| 184 | H | H | O | CF₃ | O | CH | CH₃ | OCHF₂ | 178–179° |
| 185 | H | H | O | CF₃ | O | CH | CF₃ | OCHF₂ | |
| 186 | H | H | O | CF₃ | O | CH | Cl | OCHF₂ | 139–141° |
| 187 | H | H | O | CF₃ | O | CH | OCH₃ | OCHF₂ | 186–187° |
| 188 | H | H | O | CF₃ | O | CH | C₂H₅ | OCHF₂ | |
| 189 | H | H | O | CF₃ | O | CH | CH₂F | OCHF₂ | |
| 190 | H | H | O | CF₃ | O | CH | SCH₃ | OCHF₂ | |
| 191 | H | H | O | CF₃ | O | CH | OCH₃ | SCHF₂ | |
| 192 | H | H | O | CF₃ | O | N | CH₃ | OCHF₂ | |
| 193 | H | H | O | CF₃ | O | N | OCH₃ | —O—CH₂—CH₂Cl | |
| 194 | H | H | O | CF₃ | O | N | OCH₃ | —O—CH₂—CH₂F | |
| 195 | H | H | O | CF₃ | O | N | OCH₃ | —O—CH₂—CHCl₂ | |
| 196 | H | H | O | CF₃ | O | N | OCH₃ | —O—CH₂—CHCl—CH₂Cl | |
| 197 | H | H | O | CF₃ | O | N | CH₃ | —O—CH₂—CF₃ | |
| 198 | H | H | O | CF₃ | O | CH | CH₃ | —O—CH₂—CF₃ | |
| 199 | H | H | O | CF₃ | O | CH | Cl | —O—CH₂—CF₃ | |
| 200 | H | H | O | CF₃ | O | CH | OCH₃ | —O—CH₂—CF₃ | |
| 201 | H | H | S | CHF₂ | O | CH | CH₃ | OCHF₂ | 159–160° |
| 202 | H | H | S | CHF₂ | O | CH | CF₃ | OCHF₂ | |
| 203 | H | H | S | CHF₂ | O | CH | Cl | OCHF₂ | |

TABLE 1-continued

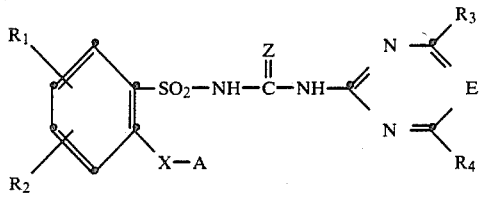

| No. | R₁ | R₂ | X | A | Z | E | R₃ | R₄ | Melting point [°C.] |
|---|---|---|---|---|---|---|---|---|---|
| 204 | H | H | S | CHF₂ | O | CH | OCH₃ | OCHF₂ | 144–146° |
| 205 | H | H | S | CHF₂ | O | CH | C₂H₅ | OCHF₂ | |
| 206 | H | H | S | CHF₂ | O | CH | CH₂F | OCHF₂ | |
| 207 | H | H | S | CHF₂ | O | CH | SCH₃ | OCHF₂ | |
| 208 | H | H | S | CHF₂ | O | CH | OCH₃ | SCHF₂ | |
| 209 | H | H | S | CHF₂ | O | N | CH₃ | OCHF₂ | |
| 210 | H | H | S | CHF₂ | O | N | OCH₃ | —O—CH₂—CH₂Cl | |
| 211 | H | H | S | CHF₂ | O | N | OCH₃ | —O—CH₂—CH₂F | |
| 212 | H | H | S | CHF₂ | O | N | OCH₃ | —O—CH₂—CHCl₂ | |
| 213 | H | H | S | CHF₂ | O | N | OCH₃ | —O—CH₂—CHCl—CH₂Cl | |
| 214 | H | H | S | CHF₂ | O | N | CH₃ | —O—CH₂—CF₃ | |
| 215 | H | H | S | CHF₂ | O | CH | CH₃ | —O—CH₂—CF₃ | |
| 216 | H | H | S | CHF₂ | O | CH | Cl | —O—CH₂—CF₃ | |
| 217 | H | H | SO₂ | CHF₂ | O | CH | CH₃ | OCHF₂ | 184–186° |
| 218 | H | H | SO₂ | CHF₂ | O | CH | CF₃ | OCHF₂ | |
| 219 | H | H | SO₂ | CHF₂ | O | CH | Cl | OCHF₂ | |
| 220 | H | H | SO₂ | CHF₂ | O | CH | OCH₃ | OCHF₂ | |
| 221 | H | H | SO₂ | CHF₂ | O | CH | C₂H₅ | OCHF₂ | |
| 222 | H | H | SO₂ | CHF₂ | O | CH | CH₂F | OCHF₂ | |
| 223 | H | H | SO₂ | CHF₂ | O | CH | SCH₃ | OCHF₂ | |
| 224 | H | H | SO₂ | CHF₂ | O | CH | OCH₃ | SCHF₂ | |
| 225 | H | H | SO₂ | CHF₂ | O | N | CH₃ | OCHF₂ | |
| 226 | H | H | SO₂ | CHF₂ | O | N | OCH₃ | —O—CH₂—CH₂Cl | |
| 227 | H | H | SO₂ | CHF₂ | O | N | OCH₃ | —O—CH₂—CH₂F | |
| 228 | H | H | SO₂ | CHF₂ | O | N | OCH₃ | —O—CH₂—CHCl₂ | |
| 229 | H | H | SO₂ | CHF₂ | O | N | OCH₃ | —O—CH₂—CHCl—CH₂Cl | |
| 230 | H | H | SO₂ | CHF₂ | O | N | CH₃ | —O—CH₂—CF₃ | |
| 231 | H | H | SO₂ | CHF₂ | O | CH | CH₃ | —O—CH₂—CF₃ | |
| 232 | H | H | SO₂ | CHF₂ | O | CH | Cl | —O—CH₂—CF₃ | |
| 233 | H | H | SO₂ | CHF₂ | O | CH | OCH₃ | —O—CH₂—CF₃ | |
| 234 | H | H | SO₂ | CHF₂ | O | N | OCH₃ | —O—CH₂—CF₃ | |
| 235 | 5-F | H | O | —CH₂—CH=CH₂ | O | CH | CH₃ | OCHF₂ | |
| 236 | 5-F | H | O | —CH₂—CH=CH₂ | O | CH | CF₃ | OCHF₂ | |
| 237 | 5-F | H | O | —CH₂—CH=CH₂ | O | CH | Cl | OCHF₂ | |
| 238 | 5-F | H | O | —CH₂—CH=CH₂ | O | CH | OCH₃ | OCHF₂ | |
| 239 | 5-F | H | O | —CH₂—CH=CH₂ | O | CH | C₂H₅ | OCHF₂ | |
| 240 | 5-F | H | O | —CH₂—CH=CH₂ | O | CH | CH₂F | OCHF₂ | |
| 241 | 5-F | H | O | —CH₂—CH=CH₂ | O | CH | SCH₃ | OCHF₂ | |
| 242 | 5-F | H | O | —CH₂—CH=CH₂ | O | CH | OCH₃ | SCHF₂ | |
| 243 | 5-F | H | O | —CH₂—CH=CH₂ | O | N | CH₃ | OCHF₂ | |
| 244 | 5-F | H | O | —CH₂—CH=CH₂ | O | N | OCH₃ | —O—CH₂—CH₂Cl | |
| 245 | 5-F | H | O | —CH₂—CH=CH₂ | O | N | OCH₃ | —O—CH₂—CH₂F | |
| 246 | 5-F | H | O | —CH₂—CH=CH₂ | O | N | OCH₃ | —O—CH₂—CHCl₂ | |
| 247 | 5-F | H | O | —CH₂—CH=CH₂ | O | N | OCH₃ | —O—CH₂—CHCl—CH₂Cl | |
| 248 | 5-F | H | O | —CH₂—CH=CH₂ | O | N | CH₃ | —O—CH₂—CF₃ | |
| 249 | 5-F | H | O | —CH₂—CH=CH₂ | O | CH | CH₃ | —O—CH₂—CF₃ | |
| 250 | 5-F | H | O | —CH₂—CH=CH₂ | O | CH | Cl | —O—CH₂—CF₃ | |
| 251 | 5-F | H | O | —CH₂—CH=CH₂ | O | CH | OCH₃ | —O—CH₂—CF₃ | |
| 252 | 5-F | H | O | CHF₂ | O | CH | CH₃ | OCHF₂ | 150–151° |
| 253 | 5-F | H | O | CHF₂ | O | CH | CF₃ | OCHF₂ | |
| 254 | 5-F | H | O | CHF₂ | O | CH | Cl | OCHF₂ | |
| 255 | 5-F | H | O | CHF₂ | O | CH | OCH₃ | OCHF₂ | |
| 256 | 5-F | H | O | CHF₂ | O | CH | C₂H₅ | OCHF₂ | |
| 257 | 5-F | H | O | CHF₂ | O | CH | CH₂F | OCHF₂ | |
| 258 | 5-F | H | O | CHF₂ | O | CH | SCH₃ | OCHF₂ | |
| 259 | 5-F | H | O | CHF₂ | O | CH | OCH₃ | SCHF₂ | |
| 260 | 5-F | H | O | CHF₂ | O | N | CH₃ | OCHF₂ | |
| 261 | 5-F | H | O | CHF₂ | O | N | OCH₃ | —O—CH₂—CH₂Cl | |
| 262 | 5-F | H | O | CHF₂ | O | N | OCH₃ | —O—CH₂—CH₂F | |
| 263 | 5-F | H | O | CHF₂ | O | N | OCH₃ | —O—CH₂—CHCl₂ | |
| 264 | 5-F | H | O | CHF₂ | O | N | OCH₃ | —O—CH₂—CHCl—CH₂Cl | |
| 265 | 5-F | H | O | CHF₂ | O | N | CH₃ | —O—CH₂—CF₃ | |
| 266 | 5-F | H | O | CHF₂ | O | CH | CH₃ | —O—CH₂—CF₃ | |
| 267 | 5-F | H | O | CHF₂ | O | CH | Cl | —O—CH₂—CF₃ | |
| 268 | 5-F | H | O | CHF₂ | O | CH | OCH₃ | —O—CH₂—CF₃ | |
| 269 | H | 6-Cl | O | CHF₂ | O | CH | CH₃ | OCHF₂ | 103–104° |
| 270 | H | 6-Cl | O | CHF₂ | O | CH | CF₃ | OCHF₂ | |
| 271 | H | 6-Cl | O | CHF₂ | O | CH | Cl | OCHF₂ | |
| 272 | H | 6-Cl | O | CHF₂ | O | CH | OCH₃ | OCHF₂ | 112–114° |

TABLE 1-continued

| No. | R₁ | R₂ | X | A | Z | E | R₃ | R₄ | Melting point [°C.] |
|---|---|---|---|---|---|---|---|---|---|
| 273 | H | 6-Cl | O | CHF$_2$ | O | CH | C$_2$H$_5$ | OCHF$_2$ | |
| 274 | H | 6-Cl | O | CHF$_2$ | O | CH | CH$_2$F | OCHF$_2$ | |
| 275 | H | 6-Cl | O | CHF$_2$ | O | CH | SCH$_3$ | OCHF$_2$ | |
| 276 | H | 6-Cl | O | CHF$_2$ | O | CH | OCH$_3$ | SCHF$_2$ | |
| 277 | H | 6-Cl | O | CHF$_2$ | O | N | CH$_3$ | OCHF$_2$ | |
| 278 | H | 6-Cl | O | CHF$_2$ | O | N | OCH$_3$ | —O—CH$_2$—CH$_2$Cl | |
| 279 | H | 6-Cl | O | CHF$_2$ | O | N | OCH$_3$ | —O—CH$_2$—CH$_2$F | |
| 280 | H | 6-Cl | O | CHF$_2$ | O | N | OCH$_3$ | —O—CH$_2$—CHCl$_2$ | |
| 281 | H | 6-Cl | O | CHF$_2$ | O | N | OCH$_3$ | —O—CH$_2$—CHCl—CH$_2$Cl | |
| 282 | H | 6-Cl | O | CHF$_2$ | O | N | CH$_3$ | —O—CH$_2$—CF$_3$ | |
| 283 | H | 6-Cl | O | CHF$_2$ | O | CH | CH$_3$ | —O—CH$_2$—CF$_3$ | |
| 284 | H | 6-Cl | O | CHF$_2$ | O | CH | Cl | —O—CH$_2$—CF$_3$ | |
| 285 | H | 6-Cl | O | CHF$_2$ | O | CH | OCH$_3$ | —O—CH$_2$—CF$_3$ | |
| 286 | H | H | O | —CH$_2$—CH$_2$—O—C$_2$H$_5$ | O | N | OCH$_3$ | —O—CH$_2$—CF$_3$ | 136–138° |
| 287 | H | H | O | —CH$_2$—CH$_2$—O—C$_2$H$_5$ | O | CH | OCH$_3$ | OCHF$_2$ | |
| 288 | H | H | O | —CH$_2$—CH$_2$—O—C$_2$H$_5$ | O | CH | CH$_3$ | OCHF$_2$ | 138–140° |
| 289 | H | H | O | —CH$_2$—CH$_2$—O—C$_2$H$_5$ | O | CH | Cl | OCHF$_2$ | |
| 290 | H | H | O | —CH$_2$—CH$_2$—O—C$_2$H$_5$ | O | CH | CH$_3$ | —O—CH$_2$—CF$_3$ | |
| 291 | H | H | O | —CF$_2$—CHFCl | O | N | OCH$_3$ | —O—CH$_2$—CF$_3$ | 173–174° |
| 292 | H | H | O | —CF$_2$—CHFCl | O | CH | OCH$_3$ | OCHF$_2$ | |
| 293 | H | H | O | —CF$_2$—CHFCl | O | CH | CH$_3$ | OCHF$_2$ | 157–158° |
| 294 | H | H | O | —CF$_2$—CHFCl | O | CH | Cl | OCHF$_2$ | |
| 295 | H | H | O | —CF$_2$—CHFCl | O | CH | CH$_3$ | —O—CH$_2$—CF$_3$ | |
| 296 | H | H | O | —CH$_2$—C(CH$_3$)=CH$_2$ | O | N | OCH$_3$ | —O—CH$_2$—CF$_3$ | |
| 297 | H | H | O | —CH$_2$—C(CH$_3$)=CH$_2$ | O | CH | OCH$_3$ | OCHF$_2$ | |
| 298 | H | H | O | —CH$_2$—C(CH$_3$)=CH$_2$ | O | CH | CH$_3$ | OCHF$_2$ | 149–151° |
| 299 | H | H | O | —CH$_2$—C(CH$_3$)=CH$_2$ | O | CH | Cl | OCHF$_2$ | |
| 300 | H | H | O | —CH$_2$—C(CH$_3$)=CH$_2$ | O | CH | CH$_3$ | —O—CH$_2$—CF$_3$ | |
| 301 | H | H | O | —CH$_2$—C(CH$_3$)=CH$_2$ | O | CH | OCH$_3$ | —O—CH$_2$—CF$_3$ | 218–219° |
| 302 | H | H | O | —CH$_2$—CHCl—CH$_2$Cl | O | N | OCH$_3$ | —O—CH$_2$—CF$_3$ | |
| 303 | H | H | O | —CH$_2$—CHCl—CH$_2$Cl | O | CH | OCH$_3$ | OCHF$_2$ | |
| 304 | H | H | O | —CH$_2$—CHCl—CH$_2$Cl | O | CH | CH$_3$ | OCHF$_2$ | |
| 305 | H | H | O | —CH$_2$—CHCl—CH$_2$Cl | O | CH | Cl | OCHF$_2$ | |
| 306 | H | H | O | —CH$_2$—CHCl—CH$_2$Cl | O | CH | CH$_3$ | —O—CH$_2$—CF$_3$ | |
| 307 | H | H | O | —CH(CH$_2$Cl)$_2$ | O | N | OCH$_3$ | —O—CH$_2$—CF$_3$ | |
| 308 | H | H | O | —CH(CH$_2$Cl)$_2$ | O | CH | OCH$_3$ | OCHF$_2$ | |
| 309 | H | H | O | —CH(CH$_2$Cl)$_2$ | O | CH | CH$_3$ | OCHF$_2$ | |
| 310 | H | H | O | —CH(CH$_2$Cl)$_2$ | O | CH | Cl | OCHF$_2$ | |
| 311 | H | H | O | —CH(CH$_2$Cl)$_2$ | O | CH | CH$_3$ | —O—CH$_2$—CF$_3$ | |
| 312 | H | H | O | —CH$_2$—CH=C(CH$_3$)$_2$ | O | N | OCH$_3$ | —O—CH$_2$—CF$_3$ | |
| 313 | H | H | O | —CH$_2$—CH=C(CH$_3$)$_2$ | O | CH | OCH$_3$ | OCHF$_2$ | |
| 314 | H | H | O | —CH$_2$—CH=C(CH$_3$)$_2$ | O | CH | CH$_3$ | OCHF$_2$ | |
| 315 | H | H | O | —CH$_2$—CH=C(CH$_3$)$_2$ | O | CH | Cl | OCHF$_2$ | |
| 316 | H | H | O | —CH$_2$—CH=C(CH$_3$)$_2$ | O | CH | CH$_3$ | —O—CH$_2$—CF$_3$ | |
| 317 | H | H | O | —CH$_2$—CH$_2$F | O | N | OCH$_3$ | —O—CH$_2$—CF$_3$ | |
| 318 | H | H | O | —CH$_2$—CH$_2$F | O | CH | OCH$_3$ | OCHF$_2$ | |
| 319 | H | H | O | —CH$_2$—CH$_2$F | O | CH | CH$_3$ | OCHF$_2$ | |
| 320 | H | H | O | —CH$_2$—CH$_2$F | O | CH | Cl | OCHF$_2$ | |
| 321 | H | H | O | —CH$_2$—CH$_2$F | O | CH | CH$_3$ | —O—CH$_2$—CF$_3$ | |
| 322 | H | H | O | —CH$_2$—CHCl$_2$ | O | N | OCH$_3$ | —O—CH$_2$—CF$_3$ | |
| 323 | H | H | O | —CH$_2$—CHCl$_2$ | O | CH | OCH$_3$ | OCHF$_2$ | |
| 324 | H | H | O | —CH$_2$—CHCl$_2$ | O | CH | CH$_3$ | OCHF$_2$ | |
| 325 | H | H | O | —CH$_2$—CHCl$_2$ | O | CH | Cl | OCHF$_2$ | |
| 326 | H | H | O | —CH$_2$—CHCl$_2$ | O | CH | CH$_3$ | —O—CH$_2$—CF$_3$ | |
| 327 | H | H | O | —CH$_2$—CCl$_3$ | O | N | OCH$_3$ | —O—CH$_2$—CF$_3$ | |
| 328 | H | H | O | —CH$_2$—CCl$_3$ | O | CH | OCH$_3$ | OCHF$_2$ | |
| 329 | H | H | O | —CH$_2$—CCl$_3$ | O | CH | CH$_3$ | OCHF$_2$ | |
| 330 | H | H | O | —CH$_2$—CCl$_3$ | O | CH | Cl | OCHF$_2$ | |
| 331 | H | H | O | —CH$_2$—CCl$_3$ | O | CH | CH$_3$ | —O—CH$_2$—CF$_3$ | |
| 332 | H | H | S | —CF$_2$—CHF$_2$ | O | N | OCH$_3$ | —O—CH$_2$—CF$_3$ | |
| 333 | H | H | S | —CF$_2$—CHF$_2$ | O | CH | OCH$_3$ | OCHF$_2$ | |
| 334 | H | H | S | —CF$_2$—CHF$_2$ | O | CH | CH$_3$ | OCHF$_2$ | |
| 335 | H | H | S | —CF$_2$—CHF$_2$ | O | CH | Cl | OCHF$_2$ | |
| 336 | H | H | S | —CF$_2$—CHF$_2$ | O | CH | CH$_3$ | —O—CH$_2$—CF$_3$ | |
| 337 | H | H | O | —CH$_2$—CH=CH—CH$_3$ | O | N | OCH$_3$ | —O—CH$_2$—CF$_3$ | 148–153° |
| 338 | H | H | O | —CH$_2$—CH=CH—CH$_3$ | O | CH | OCH$_3$ | OCHF$_2$ | |
| 339 | H | H | O | —CH$_2$—CH=CH—CH$_3$ | O | CH | CH$_3$ | OCHF$_2$ | 171–172° |
| 340 | H | H | O | —CH$_2$—CH=CH—CH$_3$ | O | CH | Cl | OCHF$_2$ | |
| 341 | H | H | O | —CH$_2$—CH=CH—CH$_3$ | O | CH | CH$_3$ | —O—CH$_2$—CF$_3$ | |

TABLE 1-continued

| No. | R$_1$ | R$_2$ | X | A | Z | E | R$_3$ | R$_4$ | Melting point [°C.] |
|---|---|---|---|---|---|---|---|---|---|
| 342 | H | H | O | —CH$_2$—CHCl—CHCl—CH$_3$ | O | N | OCH$_3$ | —O—CH$_2$—CF$_3$ | |
| 343 | H | H | O | —CH$_2$—CHCl—CHCl—CH$_3$ | O | CH | OCH$_3$ | OCHF$_2$ | |
| 344 | H | H | O | —CH$_2$—CHCl—CHCl—CH$_3$ | O | CH | CH$_3$ | OCHF$_2$ | |
| 345 | H | H | O | —CH$_2$—CHCl—CHCl—CH$_3$ | O | CH | Cl | OCHF$_2$ | |
| 346 | H | H | O | —CH$_2$—CHCl—CHCl—CH$_3$ | O | CH | CH$_3$ | —O—CH$_2$—CF$_3$ | |
| 347 | H | H | O | CF$_2$Cl | O | N | OCH$_3$ | —O—CH$_2$—CF$_3$ | |
| 348 | H | H | O | CF$_2$Cl | O | CH | OCH$_3$ | OCHF$_2$ | |
| 349 | H | H | O | CF$_2$Cl | O | CH | CH$_3$ | OCHF$_2$ | |
| 350 | H | H | O | CF$_2$Cl | O | CH | Cl | OCHF$_2$ | |
| 351 | H | H | O | CF$_2$Cl | O | CH | CH$_3$ | —O—CH$_2$—CF$_3$ | |
| 352 | H | H | O | CF$_2$Br | O | N | OCH$_3$ | —O—CH$_2$—CF$_3$ | |
| 353 | H | H | O | CF$_2$Br | O | CH | OCH$_3$ | OCHF$_2$ | |
| 354 | H | H | O | CF$_2$Br | O | CH | CH$_3$ | OCHF$_2$ | |
| 355 | H | H | O | CF$_2$Br | O | CH | Cl | OCHF$_2$ | |
| 356 | H | H | O | CF$_2$Br | O | CH | CH$_3$ | —O—CH$_2$—CF$_3$ | |
| 357 | 5-Cl | H | O | OCHF$_2$ | O | N | OCH$_3$ | —O—CH$_2$—CF$_3$ | 92–94° |
| 358 | 5-Cl | H | O | OCHF$_2$ | O | CH | OCH$_3$ | OCHF$_2$ | |
| 359 | 5-Cl | H | O | OCHF$_2$ | O | CH | CH$_3$ | OCHF$_2$ | 133–134° |
| 360 | 5-Cl | H | O | OCHF$_2$ | O | CH | Cl | OCHF$_2$ | |
| 361 | 5-Cl | H | O | OCHF$_2$ | O | CH | CH$_3$ | —O—CH$_2$—CF$_3$ | 153–155° |
| 362 | H | 6-F | O | CHF$_2$ | O | N | OCH$_3$ | —O—CH$_2$—CF$_3$ | |
| 363 | H | 6-F | O | CHF$_2$ | O | CH | OCH$_3$ | OCHF$_2$ | |
| 364 | H | 6-F | O | CHF$_2$ | O | CH | CH$_3$ | OCHF$_2$ | |
| 365 | H | 6-F | O | CHF$_2$ | O | CH | Cl | OCHF$_2$ | |
| 366 | H | 6-F | O | CHF$_2$ | O | CH | CH$_3$ | —O—CH$_2$—CF$_3$ | |
| 367 | 5-OCH$_3$ | H | O | —CH$_2$—CH=CH$_2$ | O | N | OCH$_3$ | —O—CH$_2$—CF$_3$ | |
| 368 | 5-OCH$_3$ | H | O | —CH$_2$—CH=CH$_2$ | O | CH | OCH$_3$ | OCHF$_2$ | |
| 369 | 5-OCH$_3$ | H | O | —CH$_2$—CH=CH$_2$ | O | CH | CH$_3$ | OCHF$_2$ | |
| 370 | 5-OCH$_3$ | H | O | —CH$_2$—CH=CH$_2$ | O | CH | Cl | OCHF$_2$ | |
| 371 | 5-OCH$_3$ | H | O | —CH$_2$—CH=CH$_2$ | O | CH | CH$_3$ | —O—CH$_2$—CF$_3$ | |
| 372 | H | 3-CH$_3$ | O | —CH$_2$—CH=CH$_2$ | O | N | OCH$_2$ | —O—CH$_2$—CF$_3$ | |
| 373 | H | 3-CH$_3$ | O | —CH$_2$—CH=CH$_2$ | O | CH | OCH$_3$ | OCHF$_2$ | |
| 374 | H | 3-CH$_3$ | O | —CH$_2$—CH=CH$_2$ | O | CH | CH$_3$ | OCHF$_2$ | |
| 375 | H | 3-CH$_3$ | O | —CH$_2$—CH=CH$_2$ | O | CH | Cl | OCHF$_2$ | |
| 376 | H | 3-CH$_3$ | O | —CH$_2$—CH=CH$_2$ | O | CH | CH$_3$ | —O—CH$_2$—CF$_3$ | |
| 377 | H | H | O | —CH$_2$—C(CH$_3$)Cl—CH$_2$—Cl | O | N | OCH$_3$ | —O—CH$_2$—CF$_3$ | |
| 378 | H | H | O | —CH$_2$—C(CH$_3$)Cl—CH$_2$—Cl | O | CH | OCH$_3$ | OCHF$_2$ | |
| 379 | H | H | O | —CH$_2$—C(CH$_3$)Cl—CH$_2$—Cl | O | CH | CH$_3$ | OCHF$_2$ | |
| 380 | H | H | O | —CH$_2$—C(CH$_3$)Cl—CH$_2$—Cl | O | CH | Cl | OCHF$_2$ | |
| 381 | H | H | O | —CH$_2$—C(CH$_3$)Cl—CH$_2$—Cl | O | CH | CH$_3$ | —O—CH$_2$—CF$_3$ | |
| 382 | H | H | O | —CH$_2$—CHCl$_2$ | O | N | CH$_3$ | OCHF$_2$ | |
| 383 | H | H | O | —CH$_2$—CCl$_3$ | O | N | CH$_3$ | OCHF$_2$ | |
| 384 | H | H | O | CF$_2$Cl | O | N | CH$_3$ | OCHF$_2$ | |
| 385 | H | H | O | CF$_2$Br | O | N | CH$_3$ | OCHF$_2$ | |
| 386 | H | H | S | CHF$_2$ | O | N | CH$_3$ | OCHF$_2$ | |
| 387 | H | H | S | —CF$_2$—CHF$_2$ | O | N | CH$_3$ | OCHF$_2$ | |
| 388 | H | H | SO$_2$ | CHF$_2$ | O | N | CH$_3$ | OCHF$_2$ | |
| 389 | 5-F | H | O | CHF$_2$ | O | N | CH$_3$ | OCHF$_2$ | |
| 390 | 5-F | H | O | —CH$_2$—CH=CH$_2$ | O | N | CH$_3$ | OCHF$_2$ | |
| 391 | H | 6-Cl | O | CHF$_2$ | O | N | CH$_3$ | OCHF$_2$ | |
| 392 | 5-Cl | H | O | CHF$_2$ | O | N | CH$_3$ | OCHF$_2$ | |
| 393 | H | 6-F | O | CHF$_2$ | O | N | CH$_3$ | OCHF$_2$ | |
| 394 | 5-OCH$_3$ | H | O | —CH$_2$CH=CH$_2$ | O | N | CH$_3$ | OCHF$_2$ | |
| 395 | H | 3-CH$_3$ | O | —CH$_2$CH=CH$_2$ | O | N | CH$_3$ | OCHF$_2$ | |
| 396 | H | H | O | —CH$_2$—CH$_2$—O—C$_2$H$_5$ | O | N | CH$_3$ | OCHF$_2$ | |
| 397 | H | H | O | —CH$_2$—C=C(CH$_3$)$_2$ | O | N | CH$_3$ | OCHF$_2$ | |
| 398 | H | H | O | CHF$_2$ | O | N | CH$_3$ | OCHF$_2$ | |
| 399 | H | H | O | CF$_3$ | O | N | CH$_3$ | OCHF$_2$ | |
| 400 | H | H | O | —CF$_2$—CHF$_2$ | O | N | CH$_3$ | OCHF$_2$ | |
| 401 | H | H | O | —CH$_2$—CF$_3$ | O | N | CH$_3$ | OCHF$_2$ | |
| 402 | H | H | O | —CCl=CHCl | O | N | CH$_3$ | OCHF$_2$ | |
| 403 | H | H | O | —CH$_2$—CH$_2$Cl | O | N | CH$_3$ | OCHF$_2$ | |
| 404 | H | H | O | —CH$_2$—CH$_2$—O—CH$_3$ | O | N | CH$_3$ | OCHF$_2$ | |
| 405 | H | H | O | —CF$_2$—CF$_3$ | O | N | CH$_3$ | OCHF$_2$ | |
| 406 | H | H | O | —CH$_2$—CH=CH$_2$ | O | N | CH$_3$ | OCHF$_2$ | |
| 407 | H | H | O | —CH$_2$—OCH$_3$ | O | N | CH$_3$ | OCHF$_2$ | |
| 408 | H | H | O | —CF$_2$—CHClF | O | N | CH$_3$ | OCHF$_2$ | |
| 409 | H | H | O | —CH$_2$—CH=CH—CH$_3$ | O | N | CH$_3$ | OCHF$_2$ | |
| 410 | H | H | O | —CH$_2$—CHCl—CH$_2$Cl | O | N | CH$_3$ | OCHF$_2$ | |

TABLE 1-continued

Structure: R₁, R₂ substituted phenyl with SO₂—NH—C(=Z)—NH— linked to N=C(R₃)—E—C(R₄)=N triazine/pyrimidine, with X—A substituent.

| No. | R₁ | R₂ | X | A | Z | E | R₃ | R₄ | Melting point [°C.] |
|---|---|---|---|---|---|---|---|---|---|
| 411 | H | H | O | —CH(CH₂Cl)₂ | O | N | CH₃ | OCHF₂ | |
| 412 | H | H | O | —CH₂—CH₂F | O | N | CH₃ | OCHF₂ | |
| 413 | H | H | O | —CH₂—C(CH₃)=CH₂ | O | N | CH₃ | OCHF₂ | |
| 414 | H | H | O | CHF₂ | S | N | OCH₃ | —O—CH₂—CF₃ | |
| 415 | H | H | O | CHF₂ | S | CH | CH₃ | OCHF₂ | 174–175° (decomposition) |
| 416 | H | H | O | —CH₂—CH=CH₂ | S | N | OCH₃ | —O—CH₂—CF₃ | |
| 417 | H | H | O | —CH₂—CH=CH₂ | S | CH | CH₃ | OCHF₂ | |
| 418 | H | H | O | CF₃ | S | N | OCH₃ | —O—CH₂—CF₃ | |
| 419 | H | H | O | CF₃ | S | CH | CH₃ | OCHF₂ | |
| 420 | H | H | O | —CH₂—CH₂—O—CH₃ | S | N | OCH₃ | —O—CH₂—CF₃ | |
| 421 | H | H | O | —CH₂—CH₂—O—CH₃ | S | CH | CH₃ | OCHF₂ | |
| 422 | H | H | O | CHF₂ | O | CH | OCH₃ | SCHF₂ | 120–121° |
| 423 | H | H | O | CF₃ | O | CH | OCH₃ | SCHF₂ | |
| 424 | H | H | O | —CF₂—CHF₂ | O | CH | OCH₃ | SCHF₂ | |
| 425 | H | H | O | —CH₂—CF₃ | O | CH | OCH₃ | SCHF₂ | |
| 426 | H | H | O | —CCl=CHCl | O | CH | OCH₃ | SCHF₂ | |
| 427 | H | H | O | —CH₂—CH₂Cl | O | CH | OCH₃ | SCHF₂ | |
| 428 | H | H | O | —CH₂—CH₂—O—CH₃ | O | CH | OCH₃ | SCHF₂ | |
| 429 | H | H | O | —CF₂—CF₃ | O | CH | OCH₃ | SCHF₂ | |
| 430 | H | H | O | —CH₂—CH=CH₂ | O | CH | OCH₃ | SCHF₂ | |
| 431 | H | H | O | —CH₂—O—CH₃ | O | CH | OCH₃ | SCHF₂ | |
| 432 | H | H | O | —CF₂—CHClF | O | CH | OCH₃ | SCHF₂ | |
| 433 | H | H | O | —CH₂—CH=CH—CH₃ | O | CH | OCH₃ | SCHF₂ | |
| 434 | H | H | O | —CH₂—CHCl—CH₂Cl | O | CH | OCH₃ | SCHF₂ | |
| 435 | H | H | O | —CH(CH₂Cl)₂ | O | CH | OCH₃ | SCHF₂ | |
| 436 | H | H | O | —CH₂—CH₂F | O | CH | OCH₃ | SCHF₂ | |
| 437 | H | H | O | —CH₂—C(CH₃)=CH₂ | O | CH | OCH₃ | SCHF₂ | |
| 438 | H | H | O | —CH₂—CHCl₂ | O | CH | OCH₃ | SCHF₂ | |
| 439 | H | H | O | —CH₂—CCl₃ | O | CH | OCH₃ | SCHF₂ | |
| 440 | H | H | O | CF₂Cl | O | CH | OCH₃ | SCHF₂ | |
| 441 | H | H | O | CF₂Br | O | CH | OCH₃ | SCHF₂ | |
| 442 | H | H | S | CHF₂ | O | CH | OCH₃ | SCHF₂ | |
| 443 | H | H | S | —CF₂—CHF₂ | O | CH | OCH₃ | SCHF₂ | |
| 444 | H | H | SO₂ | CHF₂ | O | CH | OCH₃ | SCHF₂ | |
| 445 | 5-F | H | O | CHF₂ | O | CH | OCH₃ | SCHF₂ | |
| 446 | 5-F | H | O | —CH₂—CH=CH₂ | O | CH | OCH₃ | SCHF₂ | |
| 447 | H | 6-Cl | O | CHF₂ | O | CH | OCH₃ | SCHF₂ | |
| 448 | 5-Cl | H | O | CHF₂ | O | CH | OCH₃ | SCHF₂ | |
| 449 | H | 6-F | O | CHF₂ | O | CH | OCH₃ | SCHF₂ | |
| 450 | 5-OCH₃ | H | O | —CH₂—CH=CH₂ | O | CH | OCH₃ | SCHF₂ | |
| 451 | H | 3-CH₃ | O | —CH₂—CH=CH₂ | O | CH | OCH₃ | SCHF₂ | |
| 452 | H | H | O | —CH₂—CH₂—OC₂H₅ | O | CH | OCH₃ | SCHF₂ | |
| 453 | H | H | O | —CH₂—C≡C(CH₃)₂ | O | CH | OCH₃ | SCHF₂ | |
| 454 | H | H | O | CHF₂ | O | CH | —O—CH₂—CF₃ | —O—CH₂—CF₃ | 165–166° |
| 455 | H | H | O | CF₃ | O | CH | —O—CH₂—CF₃ | —O—CH₂—CF₃ | |
| 456 | H | H | O | —CF₂—CHF₂ | O | CH | —O—CH₂—CF₃ | —O—CH₂—CF₃ | |
| 457 | H | H | O | —CH₂—CF₃ | O | CH | —O—CH₂—CF₃ | —O—CH₂—CF₃ | |
| 458 | H | H | O | —CCl=CHCl | O | CH | —O—CH₂—CF₃ | —O—CH₂—CF₃ | |
| 459 | H | H | O | —CH₂—CH₂Cl | O | CH | —O—CH₂—CF₃ | —O—CH₂—CF₃ | |
| 460 | H | H | O | —CH₂—CH₂—O—CH₃ | O | CH | —O—CH₂—CF₃ | —O—CH₂—CF₃ | |
| 461 | H | H | O | —CF₂—CF₃ | O | CH | —O—CH₂—CF₃ | —O—CH₂—CF₃ | |
| 462 | H | H | O | —CH₂—CH=CH₂ | O | CH | —O—CH₂—CF₃ | —O—CH₂—CF₃ | |
| 463 | H | H | O | —CH₂—O—CH₃ | O | CH | —O—CH₂—CF₃ | —O—CH₂—CF₃ | |
| 464 | H | H | O | —CF₂—CHClF | O | CH | —O—CH₂—CF₃ | —O—CH₂—CF₃ | |
| 465 | H | H | O | —CH₂—CH=CH—CH₃ | O | CH | —O—CH₂—CF₃ | —O—CH₂—CF₃ | |
| 466 | H | H | O | —CH₂—CHCl—CH₂Cl | O | CH | —O—CH₂—CF₃ | —O—CH₂—CF₃ | |
| 467 | H | H | O | —CH(CH₂Cl)₂ | O | CH | —O—CH₂—CF₃ | —O—CH₂—CF₃ | |
| 468 | H | H | O | —CH₂—CH₂F | O | CH | —O—CH₂—CF₃ | —O—CH₂—CF₃ | |
| 469 | H | H | O | —CH₂—C(CH₃)=CH₂ | O | CH | —O—CH₂—CF₃ | —O—CH₂—CF₃ | |
| 470 | H | H | O | —CH₂—CHCl₂ | O | CH | —O—CH₂—CF₃ | —O—CH₂—CF₃ | |
| 471 | H | H | O | —CH₂—CCl₃ | O | CH | —O—CH₂—CF₃ | —O—CH₂—CF₃ | |
| 472 | H | H | O | CF₂Cl | O | CH | —O—CH₂—CF₃ | —O—CH₂—CF₃ | |
| 473 | H | H | O | CF₂Br | O | CH | —O—CH₂—CF₃ | —O—CH₂—CF₃ | |
| 474 | H | H | S | CHF₂ | O | CH | —O—CH₂—CF₃ | —O—CH₂—CF₃ | |
| 475 | H | H | S | —CF₂—CHF₂ | O | CH | —O—CH₂—CF₃ | —O—CH₂—CF₃ | |
| 476 | H | H | SO₂ | CHF₂ | O | CH | —O—CH₂—CF₃ | —O—CH₂—CF₃ | |
| 477 | 5-F | H | O | CHF₂ | O | CH | —O—CH₂—CF₃ | —O—CH₂—CF₃ | |

TABLE 1-continued

Structure:

$$\text{R}_1, \text{R}_2\text{-phenyl-SO}_2\text{-NH-C(=Z)-NH-}\underset{\text{E}}{\text{pyrimidine with R}_3, \text{R}_4}$$

with X—A substituent on phenyl ring.

| No. | R₁ | R₂ | X | A | Z | E | R₃ | R₄ | Melting point [°C.] |
|---|---|---|---|---|---|---|---|---|---|
| 478 | 5-F | H | O | —CH₂—CH=CH₂ | O | CH | —O—CH₂—CF₃ | —O—CH₂—CF₃ | |
| 479 | H | 6-Cl | O | CHF₂ | O | CH | —O—CH₂—CF₃ | —O—CH₂—CF₃ | |
| 480 | 5-Cl | H | O | CHF₂ | O | CH | —O—CH₂—CF₃ | —O—CH₂—CF₃ | |
| 481 | H | 6-F | O | CHF₂ | O | CH | —O—CH₂—CF₃ | —O—CH₂—CF₃ | |
| 482 | 5-OCH₃ | H | O | —CH₂—CH=CH₂ | O | CH | —O—CH₂—CF₃ | —O—CH₂—CF₃ | |
| 483 | H | 3-CH₃ | O | —CH₂—CH=CH₂ | O | CH | —O—CH₂—CF₃ | —O—CH₂—CF₃ | |
| 484 | H | H | O | —CH₂—CH₂—O—C₂H₅ | O | CH | —O—CH₂—CF₃ | —O—CH₂—CF₃ | |
| 485 | H | H | O | —CH₂—C=C(CH₃)₂ | O | CH | —O—CH₂—CF₃ | —O—CH₂—CF₃ | |
| 486 | H | H | O | CHF₂ | O | CH | OCHF₂ | OCHF₂ | 181–182° |
| 487 | H | H | O | CF₃ | O | CH | OCHF₂ | OCHF₂ | 193–194° |
| 488 | H | H | O | —CF₂—CHF₂ | O | CH | OCHF₂ | OCHF₂ | 157–158° |
| 489 | H | H | O | —CH₂—CF₃ | O | CH | OCHF₂ | OCHF₂ | |
| 490 | H | H | O | —CCl=CHCl | O | CH | OCHF₂ | OCHF₂ | |
| 491 | H | H | O | —CH₂—CH₂Cl | O | CH | OCHF₂ | OCHF₂ | |
| 492 | H | H | O | —CH₂—CH₂—OCH₃ | O | CH | OCHF₂ | OCHF₂ | 137–138° |
| 493 | H | H | O | —CF₂—CF₃ | O | CH | OCHF₂ | OCHF₂ | 197–198° |
| 494 | H | H | O | —CH₂—CH=CH₂ | O | CH | OCHF₂ | OCHF₂ | |
| 495 | H | H | O | —CH₂OCH₃ | O | CH | OCHF₂ | OCHF₂ | |
| 496 | H | H | O | —CF₂—CHClF | O | CH | OCHF₂ | OCHF₂ | |
| 497 | H | H | O | —CH₂—CH=CH—CH₃ | O | CH | OCHF₂ | OCHF₂ | |
| 498 | H | H | O | —CH₂—CHCl—CH₂Cl | O | CH | OCHF₂ | OCHF₂ | |
| 499 | H | H | O | —CH(CH₂Cl)₂ | O | CH | OCHF₂ | OCHF₂ | |
| 500 | H | H | O | —CH₂—CH₂F | O | CH | OCHF₂ | OCHF₂ | |
| 501 | H | H | O | —CH₂—C(CH₃)=CH₂ | O | CH | OCHF₂ | OCHF₂ | |
| 502 | H | H | O | —CH₂—CHCl₂ | O | CH | OCHF₂ | OCHF₂ | |
| 503 | H | H | O | —CH₂—CCl₃ | O | CH | OCHF₂ | OCHF₂ | |
| 504 | H | H | O | CF₂Cl | O | CH | OCHF₂ | OCHF₂ | |
| 505 | H | H | O | CF₂Br | O | CH | OCHF₂ | OCHF₂ | |
| 506 | H | H | S | CHF₂ | O | CH | OCHF₂ | OCHF₂ | 157–158° |
| 507 | H | H | S | —CF₂—CHF₂ | O | CH | OCHF₂ | OCHF₂ | |
| 508 | H | H | SO₂ | CHF₂ | O | CH | OCHF₂ | OCHF₂ | |
| 509 | 5-F | H | O | CHF₂ | O | CH | OCHF₂ | OCHF₂ | |
| 510 | 5-F | H | O | —CH₂—CH=CH₂ | O | CH | OCHF₂ | OCHF₂ | |
| 511 | H | 6-Cl | O | CHF₂ | O | CH | OCHF₂ | OCHF₂ | |
| 512 | 5-Cl | H | O | CHF₂ | O | CH | OCHF₂ | OCHF₂ | |
| 513 | H | 6-F | O | CHF₂ | O | CH | OCHF₂ | OCHF₂ | |
| 514 | 5-OCH₃ | H | O | —CH₂—CH=CH₂ | O | CH | OCHF₂ | OCHF₂ | |
| 515 | H | 3-CH₃ | O | —CH₂—CH=CH₂ | O | CH | OCHF₂ | OCHF₂ | |
| 516 | H | H | O | —CH₂—CH₂—O—C₂H₅ | O | CH | OCHF₂ | OCHF₂ | |
| 517 | H | H | O | —CH₂—C=C(CH₃)₂ | O | CH | OCHF₂ | OCHF₂ | |
| 518 | H | H | O | CHF₂ | O | N | CH₃ | —O—CH₂—CH₂Cl | 81° (decomposition) |
| 519 | H | H | O | CHF₂ | O | N | CH₃ | —O—CH₂—CCl₃ | 141–142° |
| 520 | H | H | O | CHF₂ | O | N | CH₃ | —O—CF₂—CHFCl | 167–168° |
| 521 | H | H | O | CHF₂ | O | CH | CH₃ | —O—CF₂—CHF₂ | 151–152° |
| 522 | H | H | O | CHF₂ | O | CH | CH₃ | —O—CF₂—CHFBr | |
| 523 | H | H | O | CHF₂ | O | CH | OCH₃ | —O—CF₂—CHF₂ | 137–138° |
| 524 | H | H | O | CHF₂ | O | CH | OCH₃ | —O—CF₂—CHFCl | 125–126° |
| 525 | H | H | O | CHF₂ | O | CH | OCH₃ | —O—CF₂—CHF—CF₃ | |
| 526 | H | H | O | CHF₂ | O | CH | Cl | —O—CF₂—CHF₂ | |
| 527 | H | H | O | CHF₂ | O | CH | Cl | —O—CF₂—CHFCl | 150–151° |
| 528 | H | H | O | CHF₂ | O | N | CH₃ | —O—CF₂—CHF₂ | |
| 529 | H | H | O | CHF₂ | O | N | CH₃ | —O—CF₂—CHFCl | |
| 530 | H | H | O | CHF₂ | O | N | OCH₃ | —O—CF₂—CHF₂ | |
| 531 | H | H | O | CHF₂ | O | N | OCH₃ | —O—CF₂—CHFCl | |
| 532 | H | H | O | CHF₂ | O | N | OCH₃ | —O—CF₂—CHFBr | |
| 533 | H | H | O | CHF₂ | O | N | OCH₃ | —O—CF₂—CHF—CF₃ | |
| 534 | H | H | O | CHF₂ | O | N | C₂H₅ | —O—CF₂—CHF₂ | |
| 535 | H | H | O | CF₃ | O | CH | CH₃ | —O—CF₂—CHFCl | |
| 536 | H | H | O | CF₃ | O | CH | CH₃ | —O—CF₂—CHF₂ | |
| 537 | H | H | O | CF₃ | O | CH | CH₃ | —O—CF₂—CHFBr | |
| 538 | H | H | O | CF₃ | O | CH | OCH₃ | —O—CF₂—CHF₂ | |
| 539 | H | H | O | CF₃ | O | CH | OCH₃ | —O—CF₂—CHFCl | |
| 540 | H | H | O | CF₃ | O | CH | OCH₃ | —O—CF₂—CHF—CF₃ | |
| 541 | H | H | O | CF₃ | O | CH | Cl | —O—CF₂—CHF₂ | |
| 542 | H | H | O | CF₃ | O | CH | Cl | —O—CF₂—CHFCl | |
| 543 | H | H | O | CF₃ | O | N | CH₃ | —O—CF₂—CHF₂ | |
| 544 | H | H | O | CF₃ | O | N | CH₃ | —O—CF₂—CHFCl | |

TABLE 1-continued

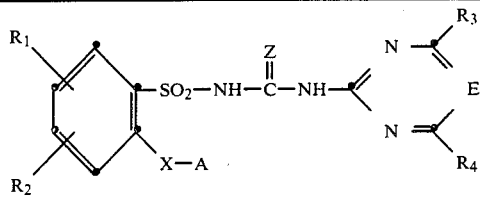

| No. | R₁ | R₂ | X | A | Z | E | R₃ | R₄ | Melting point [°C.] |
|---|---|---|---|---|---|---|---|---|---|
| 545 | H | H | O | CF₃ | O | N | OCH₃ | —O—CF₂—CHF₂ | |
| 546 | H | H | O | CF₃ | O | N | OCH₃ | —O—CF₂—CHFCl | |
| 547 | H | H | O | CF₃ | O | N | OCH₃ | —O—CF₂—CHFBr | |
| 548 | H | H | O | CF₃ | O | N | OCH₃ | —O—CF₂—CHF—CF₃ | |
| 549 | H | H | O | CF₃ | O | N | C₂H₅ | —O—CF₂—CHF₂ | |
| 550 | H | H | O | —CH₂—CH=CH₂ | O | CH | CH₃ | —O—CF₂—CHFCl | |
| 551 | H | H | O | —CH₂—CH=CH₂ | O | CH | CH₃ | —O—CF₂—CHF₂ | |
| 552 | H | H | O | —CH₂—CH=CH₂ | O | CH | CH₃ | —O—CF₂—CHFBr | |
| 553 | H | H | O | —CH₂—CH=CH₂ | O | CH | OCH₃ | —O—CF₂—CHF₂ | |
| 554 | H | H | O | —CH₂—CH=CH₂ | O | CH | OCH₃ | —O—CF₂—CHFCl | |
| 555 | H | H | O | —CH₂—CH=CH₂ | O | CH | OCH₃ | —O—CF₂—CHF—CF₃ | |
| 556 | H | H | O | —CH₂—CH=CH₂ | O | CH | Cl | —O—CF₂—CHF₂ | |
| 557 | H | H | O | —CH₂—CH=CH₂ | O | CH | Cl | —O—CF₂—CHFCl | |
| 558 | H | H | O | —CH₂—CH=CH₂ | O | N | CH₃ | —O—CF₂—CHF₂ | |
| 559 | H | H | O | —CH₂—CH=CH₂ | O | N | CH₃ | —O—CF₂—CHFCl | |
| 560 | H | H | O | —CH₂—CH=CH₂ | O | N | OCH₃ | —O—CF₂—CHF₂ | |
| 561 | H | H | O | —CH₂—CH=CH₂ | O | N | OCH₃ | —O—CF₂—CHFCl | |
| 562 | H | H | O | —CH₂—CH=CH₂ | O | N | OCH₃ | —O—CF₂—CHFBr | |
| 563 | H | H | O | —CH₂—CH=CH₂ | O | N | OCH₃ | —O—CF₂—CHF—CF₃ | |
| 564 | H | H | O | —CH₂—CH=CH₂ | O | N | C₂H₅ | —O—CF₂—CHF₂ | |
| 565 | H | H | S | CHF₂ | O | CH | CH₃ | —O—CF₂—CHFCl | |
| 566 | H | H | S | CHF₂ | O | CH | CH₃ | —O—CF₂—CHF₂ | |
| 567 | H | H | S | CHF₂ | O | CH | CH₃ | —O—CF₂—CHFBr | |
| 568 | H | H | S | CHF₂ | O | CH | CH₃ | —O—CF₂—CHF₂ | |
| 569 | H | H | S | CHF₂ | O | CH | OCH₃ | —O—CF₂—CHFCl | |
| 570 | H | H | S | CHF₂ | O | CH | OCH₃ | —O—CF₂—CHF—CF₃ | |
| 571 | H | H | S | CHF₂ | O | CH | Cl | —O—CF₂—CHF₂ | |
| 572 | H | H | S | CHF₂ | O | CH | Cl | —O—CF₂—CHFCl | |
| 573 | H | H | S | CHF₂ | O | N | CH₃ | —O—CF₂—CHF₂ | |
| 574 | H | H | S | CHF₂ | O | N | CH₃ | —O—CF₂—CHFCl | |
| 575 | H | H | S | CHF₂ | O | N | OCH₃ | —O—CF₂—CHF₂ | |
| 576 | H | H | S | CHF₂ | O | N | OCH₃ | —O—CF₂—CHFCl | |
| 577 | H | H | S | CHF₂ | O | N | OCH₃ | —O—CF₂—CHFBr | |
| 578 | H | H | S | CHF₂ | O | N | OCH₃ | —O—CF₂—CHF—CF₃ | |
| 579 | H | H | S | CHF₂ | O | N | C₂H₅ | —O—CF₂—CHF₂ | |
| 580 | H | H | O | —CCl=CHCl | O | CH | CH₃ | —O—CF₂—CHFCl | |
| 581 | H | H | O | —CCl=CHCl | O | CH | CH₃ | —O—CF₂—CHF₂ | |
| 582 | H | H | O | —CCl=CHCl | O | CH | CH₃ | —O—CF₂—CHFBr | |
| 583 | H | H | O | —CCl=CHCl | O | CH | OCH₃ | —O—CF₂—CHF₂ | |
| 584 | H | H | O | —CCl=CHCl | O | CH | OCH₃ | —O—CF₂—CHFCl | |
| 585 | H | H | O | —CCl=CHCl | O | CH | OCH₃ | —O—CF₂—CHF—CF₃ | |
| 586 | H | H | O | —CCl=CHCl | O | CH | Cl | —O—CF₂—CHF₂ | |
| 587 | H | H | O | —CCl=CHCl | O | CH | Cl | —O—CF₂—CHFCl | |
| 588 | H | H | O | —CCl=CHCl | O | N | CH₃ | —O—CF₂—CHF₂ | |
| 589 | H | H | O | —CCl=CHCl | O | N | CH₃ | —O—CF₂—CHFCl | |
| 590 | H | H | O | —CCl=CHCl | O | N | OCH₃ | —O—CF₂—CHF₂ | |
| 591 | H | H | O | —CCl=CHCl | O | N | OCH₃ | —O—CF₂—CHFCl | |
| 592 | H | H | O | —CCl=CHCl | O | N | OCH₃ | —O—CF₂—CHFBr | |
| 593 | H | H | O | —CCl=CHCl | O | N | OCH₃ | —O—CF₂—CHF—CF₃ | |
| 594 | H | H | O | —CCl=CHCl | O | N | C₂H₅ | —O—CF₂—CHF₂ | |
| 595 | H | H | O | C₂H₅ | O | CH | CH₃ | —O—CF₂—CHF₂ | |
| 596 | H | H | O | C₂H₅ | O | CH | OCH₃ | —O—CF₂—CHF₂ | |
| 597 | H | H | O | C₂H₅ | O | CH | OCH₃ | —O—CF₂—CHFCl | |
| 598 | H | H | O | C₂H₅ | O | CH | CH₃ | —O—CF₂—CHFCl | |
| 599 | H | H | O | C₂H₅ | O | N | OCH₃ | —O—CF₂—CHFCl | |
| 600 | H | H | O | C₂H₅ | O | N | OCH₃ | —O—CF₂—CF₂H | |
| 601 | H | H | O | —CH₂—CH₂Cl | O | CH | CH₃ | —O—CF₂—CHFCl | |
| 602 | H | H | O | —CH₂—CH₂Cl | O | CH | OCH₃ | —O—CF₂—CHF₂ | |
| 603 | H | H | O | —CH₂—CH₂Cl | O | N | CH₃ | —O—CF₂—CHF₂ | |
| 604 | H | H | O | —CH₂—CH₂Cl | O | N | OCH₃ | —O—CF₂—CHF₂ | |
| 605 | H | H | O | —CH₂—CH₂Cl | O | N | CH₃ | —O—CF₂—CHFCl | |
| 606 | H | H | O | —CH₂—CH₂Cl | O | CH | CH₃ | —O—CF₂—CHF₂ | |
| 607 | H | H | O | —CH₂—CH₂Cl | O | CH | OCH₃ | —O—CF₂—CHFCl | |
| 608 | H | H | O | —O—(CH₂)₂—OCH₃ | O | CH | CH₃ | —O—CF₂—CHFCl | |
| 609 | H | H | O | —O—(CH₂)₂—OCH₃ | O | CH | CH₃ | —O—CF₂—CHF₂ | |
| 610 | H | H | O | —O—(CH₂)₂—OCH₃ | O | CH | OCH₃ | —O—CF₂—CHF₂ | |
| 611 | H | H | O | —O—(CH₂)₂—OCH₃ | O | CH | OCH₃ | —O—CF₂—CHFCl | |
| 612 | H | H | O | —O—(CH₂)₂—OCH₃ | O | N | CH₃ | —O—CF₂—CHFCl | |
| 613 | H | H | O | —O—(CH₂)₂—OCH₃ | O | N | OCH₃ | —O—CF₂—CHFCl | |

TABLE 1-continued

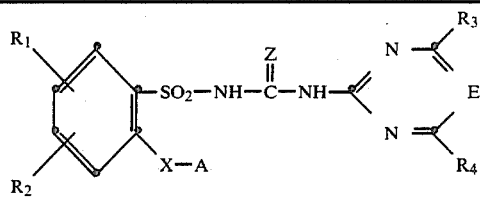

| No. | R$_1$ | R$_2$ | X | A | Z | E | R$_3$ | R$_4$ | Melting point [°C.] |
|---|---|---|---|---|---|---|---|---|---|
| 614 | H | H | O | —(CH$_2$)$_2$—S—CH$_3$ | O | CH | CH$_3$ | OCHF$_2$ | 167-68° |
| 615 | H | H | O | —(CH$_2$)$_2$—S—CH$_3$ | O | CH | OCH$_3$ | OCHF$_2$ | |
| 616 | H | H | O | —(CH$_2$)$_2$—S—CH$_3$ | O | N | OCH$_3$ | —O—CH$_2$—CF$_3$ | |
| 617 | H | H | O | —(CH$_2$)$_2$—S—CH$_3$ | O | CH | Cl | OCHF$_2$ | |
| 618 | H | H | O | —(CH$_2$)$_2$—S—CH$_3$ | O | CH | CH$_3$ | —O—CH$_2$—CF$_3$ | |
| 619 | H | H | O | —(CH$_2$)$_2$—S—CH$_3$ | O | CH | OCHF$_2$ | OCHF$_2$ | |
| 620 | H | H | O | —(CH$_2$)$_2$—S—CH$_3$ | O | CH | CH$_3$ | —O—CF$_2$—CHF$_2$ | |
| 621 | H | H | O | —(CH$_2$)$_2$—S—CH$_3$ | O | CH | OCH$_3$ | —O—CF$_2$—CHF$_2$ | |
| 622 | H | H | O | —(CH$_2$)$_2$—S—CH$_3$ | O | N | OCH$_3$ | —O—CF$_2$—CHF$_2$ | |
| 623 | H | H | O | —(CH$_2$)$_2$—SO—CH$_3$ | O | CH | CH$_3$ | OCHF$_2$ | |
| 624 | H | H | O | —(CH$_2$)$_2$—SO—CH$_3$ | O | CH | OCH$_3$ | OCHF$_2$ | |
| 625 | H | H | O | —(CH$_2$)$_2$—SO—CH$_3$ | O | CH | Cl | OCHF$_2$ | |
| 626 | H | H | O | —(CH$_2$)$_2$—SO—CH$_3$ | O | CH | CH$_3$ | —O—CH$_2$—CF$_3$ | |
| 627 | H | H | O | —(CH$_2$)$_2$—SO—CH$_3$ | O | CH | OCHF$_2$ | OCHF$_2$ | |
| 628 | H | H | O | —(CH$_2$)$_2$—SO—CH$_3$ | O | CH | CH$_3$ | —O—CF$_2$—CHF$_2$ | |
| 629 | H | H | O | —(CH$_2$)$_2$—SO—CH$_3$ | O | CH | OCH$_3$ | —O—CF$_2$—CHF$_2$ | |
| 630 | H | H | O | —(CH$_2$)$_2$—SO—CH$_3$ | O | N | OCH$_3$ | —O—CH$_2$—CF$_3$ | |
| 631 | H | H | O | —(CH$_2$)$_2$—SO—CH$_3$ | O | CH | OCH$_3$ | —O—CF$_2$—CHF$_2$ | |
| 632 | H | H | O | —(CH$_2$)$_2$—SO$_2$—CH$_3$ | O | CH | CH$_3$ | OCHF$_2$ | |
| 633 | H | H | O | —(CH$_2$)$_2$—SO$_2$—CH$_3$ | O | CH | OCH$_3$ | OCHF$_2$ | |
| 634 | H | H | O | —(CH$_2$)$_2$—SO$_2$—CH$_3$ | O | CH | Cl | OCHF$_2$ | |
| 635 | H | H | O | —(CH$_2$)$_2$—SO$_2$—CH$_3$ | O | CH | CH$_3$ | —O—CH$_2$—CF$_3$ | |
| 636 | H | H | O | —(CH$_2$)$_2$—SO$_2$—CH$_3$ | O | CH | OCHF$_2$ | OCHF$_2$ | |
| 637 | H | H | O | —(CH$_2$)$_2$—SO$_2$—CH$_3$ | O | CH | CH$_3$ | —O—CF$_2$—CHF$_2$ | |
| 638 | H | H | O | —(CH$_2$)$_2$—SO$_2$—CH$_3$ | O | CH | OCH$_3$ | —O—CF$_2$—CHF$_2$ | |
| 639 | H | H | O | —(CH$_2$)$_2$—SO$_2$—CH$_3$ | O | N | OCH$_3$ | —O—CH$_2$—CF$_3$ | |
| 640 | H | H | O | —(CH$_2$)$_2$—SO$_2$—CH$_3$ | O | CH | OCH$_3$ | —O—CF$_2$—CHF$_2$ | |

TABLE 2

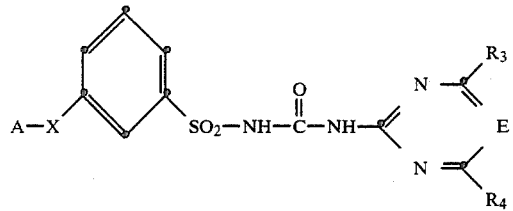

| No. | X | A | E | R$_3$ | R$_4$ | Melting point [°C.] |
|---|---|---|---|---|---|---|
| 701 | O | CHF$_2$ | CH | OCH$_3$ | OCHF$_2$ | 148-149° |
| 702 | O | CHF$_2$ | CH | CH$_3$ | OCHF$_2$ | |
| 703 | O | CHF$_2$ | CH | Cl | OCHF$_2$ | |
| 704 | O | CHF$_2$ | CH | CH$_3$ | —O—CH$_2$—CF$_3$ | |
| 705 | O | CHF$_2$ | N | OCH$_3$ | —O—CH$_2$—CF$_3$ | |
| 706 | O | —CF$_2$—CHF$_2$ | CH | OCH$_3$ | OCHF$_2$ | |
| 707 | O | —CF$_2$—CHF$_2$ | CH | CH$_3$ | OCHF$_2$ | |
| 708 | O | —CF$_2$—CHF$_2$ | CH | Cl | OCHF$_2$ | |
| 709 | O | —CF$_2$—CHF$_2$ | CH | CH$_3$ | —O—CH$_2$—CF$_3$ | |
| 710 | O | —CF$_2$—CHF$_2$ | N | OCH$_3$ | —O—CH$_2$—CF$_3$ | |

FORMULATION EXAMPLES

Example 8

Formulation examples for active substances of the formula I (%=percent by weight)

| (a) Wettable powder | (a) | (b) | (c) |
|---|---|---|---|
| active substance | 20% | 60% | 0.5% |
| Na lignin-sulfonate | 5% | 5% | 5% |
| Na lauryl-sulfate | 3% | — | — |
| Na diisobutylnaphthalene-sulfonate | — | 6% | 6% |
| octylphenol-polyethylene glycol ether (7-8 mols of ethylene oxide) | — | 2% | 2% |
| highly disperse silica | 5% | 27% | 27% |
| kaolin | 67% | — | — |
| sodium chloride | — | — | 59.5% |

The active substance is mixed thoroughly with the adjuvants and the mixture is ground well in a suitable mill. Wettable powders are obtained which can be diluted with water to give suspensions of any desired concentration.

| (b) Emulsion concentrate | (a) | (b) |
|---|---|---|
| active substance | 10% | 1% |
| octylphenol-polyethylene glycol ether (4–5 mols of ethylene oxide) | 3% | 3% |
| Ca dodecylbenzenesulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of any desired concentration can be prepared from this concentrate by dilution with water.

| (c) Dusts | (a) | (b) |
|---|---|---|
| active substance | 0.1% | 1% |
| talc | 99.9% | — |
| kaolin | — | 99% |

Ready-to-use dusts are obtained by mixing the active substance with the carrier and grinding the mixture on a suitable mill.

| (d) Extruded granules | (a) | (b) |
|---|---|---|
| active substance | 10% | 1% |
| Na lignin-sulfonate | 2% | 2% |
| carboxymethylcellulose | 1% | 1% |
| kaolin | 87% | 96% |

The active substance is mixed with the adjuvants, and the mixture is ground and moistened with water. This mixture is extruded and the extruded material is then dried in a stream of air.

| (e) Coated granules | |
|---|---|
| active substance | 3% |
| polyethylene glycol (molecular weight 200) | 3% |
| kaolin | 94% |

The finely ground active substance is uniformly applied to the kaolin, moistened with polyethylene glycol, in a mixer. This gives dust-free coated granules.

| (f) Suspension concentrate | (a) | (b) |
|---|---|---|
| active substance | 40% | 5% |
| ethylene glycol | 10% | 10% |
| nonylphenol-polyethylene glycol ether (15 mols of ethylene oxide) | 6% | 1% |
| Na lignin-sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active substance is intimately mixed with the adjuvants to give a suspension concentrate from which suspensions of any desired concentration can be prepared by dilution with water.

| (g) Salt solution | |
|---|---|
| active substance | 5% |
| isopropylamine | 1% |
| octylphenol-polyethylene glycol ether (78 mols of ethylene oxide) | 3% |
| water | 91% |

BIOLOGICAL EXAMPLES

Example 9

Demonstration of the herbicidal action before emergence of the plants

Plant seeds are sown in flowerpots 12–15 cm in diameter in a greenhouse. Immediately thereafter, the soil surface is treated with an aqueous dispersion or solution of the active substances. Concentrations of 4 kg of active substance per hectare are used. The pots are then kept at a temperature of 22°–25° C. and at 50–70% relative atmospheric humidity in the greenhouse. The experiment is evaluated after 3 weeks, and the action on the experimental plants is rated according to the following scale:

1: Plants have not germinated or have been totally destroyed
2–3: Very powerful action
4–6: Moderate action
7–8: Weak action
9: No action (as untreated control).

PRE-EMERGENCE ACTION

Amount used: 4 kg of active substance/hectare

| Compound No. | Avena | Setaria | Sinapis | Stellaria |
|---|---|---|---|---|
| 2 | 4 | 3 | 2 | 2 |
| 31 | 2 | 1 | 2 | 2 |

Example 10

Demonstration of the selectivity in pre-emergence use

In the same experimental design as in Example 9, a larger number of plant seeds are treated with various amounts of active substance. The experiment was evaluated according to the same scale.

| | Pre-emergence action: | | | | | |
|---|---|---|---|---|---|---|
| Action kg of active substance. applied/ha of test plants | Compound No. 1 | | Compound No. 6 | | Compound No. 25 | |
| | 0.06 | 0.03 | 0.06 | 0.03 | 0.06 | 0.03 |
| Wheat | 9 | 9 | 7 | 9 | 9 | 9 |
| Maize | 2 | 6 | 6 | 7 | 9 | 9 |
| Alopecurus myos. | 2 | 2 | 4 | 6 | 6 | 6 |
| Cyperus escul. | 5 | 6 | 2 | 2 | 4 | 4 |
| Abutilon | 3 | 3 | 2 | 3 | 3 | 3 |
| Chenopodium sp. | 3 | 3 | 2 | 2 | 3 | 3 |
| Ipomoea | 4 | 8 | 2 | 2 | 8 | 9 |
| Sinapis | 2 | 2 | 2 | 2 | 2 | 2 |
| Galium | 4 | 4 | 2 | 2 | 2 | 3 |
| Viola tricolor | 2 | 2 | 1 | 1 | 2 | 3 |

Example 11

Demonstration of the herbicidal action after emergence of the plants (contact action)

A number of both monocotyledonous and dicotyledonous weeds and crop plants are sprayed, after emergence, in the 4- to 6-leaf stage with an aqueous active substance dispersion in dosages of 4 kg of active substance/ha, and are then kept at 24° to 26° C. and at 45–60% relative atmospheric humidity. The experiment is evaluated 15 days after the treatment and the plants are rated according to the same scale as in the pre-emergence experiment.

POST-EMERGENCE ACTION

Amount applied: 4 kg of active substance/hectare

| Compound No. | Avena | Setaria | Lolium | Solanum | Sinapis | Stellaria | Phaseolus |
|---|---|---|---|---|---|---|---|
| 2 | 5 | 2 | 2 | 2 | 2 | 2 | 3 |
| 31 | 2 | 3 | 3 | 2 | 2 | 3 | 3 |

Example 12

Demonstration of the selectivity in post-emergence use

In the same experimental design as in Example 11, a larger number of plants are treated with various amounts of active substance. The evaluation was carried out according to the scale given in Example 9.

| | Post-emergence action | | | |
|---|---|---|---|---|
| Action kg of active substance applied/ha of test plants | Compound No. 6 | | Compound No. 25 | |
| | 0.06 | 0.03 | 0.06 | 0:03 |
| Wheat | 8 | 9 | 9 | 9 |
| Maize | 9 | 9 | 9 | 9 |
| Dry rice | 7 | 9 | 9 | 9 |
| *Cyperus escul.* | 3 | 4 | 4 | 4 |
| Cotton | 9 | 9 | 9 | 9 |
| Xanthium sp. | 2 | 2 | 1 | 1 |
| Chenopodium sp. | 3 | 3 | 9 | 9 |
| Sinapis | 2 | 3 | 3 | 4 |
| Galium aparine | 1 | 2 | 6 | 7 |
| Viola tricolor | 3 | 4 | 3 | 4 |

Example 13

Demonstration of the inhibition of sprouting of stored potatoes

A number of commercially available potatoes of the "Urgenta" variety without sprouts are washed and dried. The potatoes are then immersed in active substance emulsions of various concentrations, in each case for one minute, and are then laid out on filter paper in plastic dishes and kept at temperatures of 14° and 21° C. in the dark at 50% relative atmospheric humidity. Evaluation was effected 34 days after the application. At the same time, the weight loss of the tubers and the weight of sprouts were determined, in comparison with the untreated control. In this experiment, the compounds according to the invention showed complete prevention of sprouting. At the same time, the weight loss of the potatoes was less than 10% of the weight loss of the control potatoes.

Example 14

Demonstration of the inhibition of growth in tropical leguminosae cover crops

Test plants of the *Psophocarpus palustris* and *Centrosema pubescens* variety are grown, from cuttings, in plastic dishes containing a soil/peat/sand mixture (1:1:1). After the small plants have taken root, they are repotted in 9 cm pots and watered as required. Further cultivation of the plants takes place in a greenhouse at a daytime temperature of 27° C. and a nighttime temperature of 21° C., with a mean period of light of 14 hours (6000 lux) and at an atmospheric humidity of 70%. The test plants are cut back to a height of about 15 cm and, 7 days thereafter, are sprayed with a spray liquor of the active substance (calculated as 0.3 or 3 kg of active substance per hectare). 4 weeks after the application, the growth of the treated plants is compared with that of control plants which have been pruned but not treated. In this experiment, the plants treated with the active substances of the formula I show a distinct reduction in new additional growth (less than 20% of the new additional growth of untreated control plants) without the experimental plants thereby being damaged.

Example 15

Demonstration of pre-emergence selectivity in soybean crops

The experimental plants are sown in sandy/loamy arable soil in plastic containers having a capacity of 30 l (60×30×25 cm), and are covered with a layer of soil 1–2 cm deep and watered with water. After one day, the active substance is applied in the form of an aqueous spray liquor in an amount corresponding to 500 l/ha and in concentrations corresponding to 60 g/ha and 30 g/ha. The containers are then kept in a greenhouse at temperatures of 20°–25° C. and are watered as required. After 33 days, the experiment is evaluated and the plants are rated according to the same scale as in Example 9.

PRE-EMERGENCE ACTION IN SOYBEAN CROPS

Active substance No. 31

| | Amount applied | |
|---|---|---|
| Experimental plants | 0.06 kg/ha | 0.03 kg/ha |
| Soybean | 7 | 8 |
| *Amaranthus ret.* | 2 | 3 |
| *Ipomoea p.* | 3 | 4 |
| *Portulaca o.* | 1 | 2 |
| *Brachiaria pl.* | 3 | 4 |
| *Xanthium can.* | 3 | 3 |

Example 16

Growth regulation of soybeans

Soybeans of the "Hark" variety are sown in a soil/peat/sand mixture in the ratio 6:3:1 in plastic containers and are placed in a climatically controlled chamber. As a result of optimum selection of the temperature, illumination, addition of fertiliser and watering, the plants have developed as far as the 5-6 trifoliate-leaf stage after about 5 weeks. At this point in time, the plants are sprayed with the aqueous liquor of an active substance of the formula I until thoroughly wet. The concentration is up to 100 g of active substance/ha. The evaluation is effected about 5 weeks after application of the active substance. The active substances of the formula I according to the invention cause a noticeable increase in the number and weight of silicles on the main stem in comparison with the untreated control plants.

GROWTH-REGULATING ACTION IN SOYBEAN CROPS

Active substance No. 31

| Amount applied g/ha | Height of plants in % relative to the control | Number of silicles on the main stem in % relative to the control | Weight of silicles on the main stem in % relative to the control |
|---|---|---|---|
| 3 | 100 | 130 | 124 |
| 10 | 99 | 115 | 106 |
| 30 | 99 | 110 | 100 |
| 100 | 89 | 115 | 112 |

What is claimed is:

1. A compound of the formula:

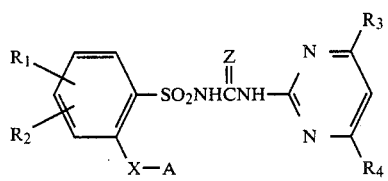

wherein
Z is O or S;
X is O, S, SO or SO$_2$;
A is (i) halogenated alkyl or halogenated alkenyl of up to 6 carbon atoms or (ii) alkyl or alkenyl or up to 6 carbon atoms substituted with an unhalogenated or halogenated alkoxy, alkylthio, alkylsulfinyl or alkylsulfonyl group of up to 4 carbon atoms;
R$_1$ is hydrogen, halo, alkyl of up to 5 carbon atoms, or R$_5$—Y— in which Y is O, S, SO or SO$_2$; and R$_5$ is an alkyl, alkenyl or alkynyl group of up to 5 carbon atoms;
R$_2$ is hydrogen, halo, alkyl of up to 5 carbon atoms, haloalkyl of up to 5 carbon atoms, R$_5$—Y— in which Y and R$_5$ are as defined above, nitro, R$_6$O—CO— or R$_7$R$_8$NCO—, in which R$_6$ is an alkyl, alkenyl, or alkynyl group of up to 5 carbon atoms; and
each of R$_7$ and R$_8$ are hydrogen or an alkyl, alkenyl or alkynyl group of up to 5 carbon atoms;
R$_3$ is hydrogen, halo, alkyl of up to 4 carbon atoms, alkoxy of up to 4 carbon atoms, alkylthio of up to 4 carbon atoms, haloalkyl of up to 4 carbon atoms, haloalkoxy of up to 4 carbon atoms, or alkoxyalkyl of up to 4 carbon atoms; and
R$_4$ is halogenated alkoxy or halogenated alkylthio of up to 4 carbon atoms.

2. N-(2-Difluoromethoxyphenylsulfonyl)-N'-(4-difluoromethoxy-6-methylpyrimidin-2-yl)-urea of claim 1.

3. A herbicidal and growth-regulating composition which comprises an effective amount of at least one compound according to claim 1 together with a suitable carrier therefor.

4. A compound of claim 1, in which Z is oxygen.

5. A compound of claim 1, in which X is oxygen.

6. A compound of claim 1, in which the radicals R$_3$ and R$_4$ together contain not more than 4 carbon atoms.

7. A compound of claim 1, in which X and Z are oxygen, and the radical —X—A is in the 2-position relative to the sulfonyl group.

8. A compound of claim 7, in which the radicals R$_3$ and R$_4$ together contain not more than 4 carbon atoms.

9. A compound of claim 8, in which R$_4$ is halogenoethoxy.

10. A compound of claim 8, in which R$_4$ is halogenomethoxy.

11. A compound of claim 9, in which R$_4$ is 2,2,2-trifluoroethoxy.

12. A compound of claim 10, in which R$_4$ is difluoromethoxy.

13. N-(2-Difluoromethoxyphenyl-sulfonyl)-N'-(4-difluoromethoxy-6-methylpyrimidin-2-yl)-urea of claim 1.

14. A method of controlling undesired plant growth, which method comprises applying thereto or to the locus thereof a herbicidally effective amount of a compound of claim 1.

15. A method of suppressing plant growth, which method comprises applying thereto or to the locus thereof an effective amount of a compound of claim 1.

16. A method of claim 14 for selectively controlling weeds in crops of cultivated plants which method comprises applying a compound of claim 1 pre-emergence or post-emergence.

17. A method of claim 16 for controlling weeds in crops of cereals, maize, rice or cotton.

18. A method of claim 16 for controlling weeds in crops of soybeans.

19. A method of claim 15 for suppressing plant growth beyond the two-leaf stage which method comprises applying the compound pre-emergence.

20. A method of regulating plant growth in order to achieve greater yields, which method comprises applying thereto or the locus thereof an effective amount of a compound of claim 1.

21. A method of claim 20 for regulating plant growth in crops of soybeans.

22. A method of claim 15 for suppressing the growth of cover crop leguminosae.

23. N-(2-Trifluoromethoxyphenyl-sulfonyl)-N'-(4-difluoromethoxy-6-methyl-pyrimidin-2-yl)-urea of claim 1.

24. A compound of the formula:

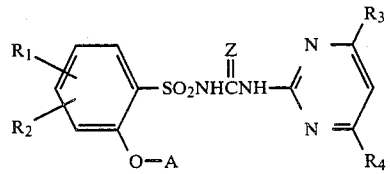

wherein
Z is O or S;
A is alkenyl of up to 6 carbon atoms;
R$_1$ is hydrogen, halo, alkyl of up to 5 carbon atoms, or R$_5$—Y— in which Y is O, S, SO or SO$_2$; and R$_5$ is an alkyl, alkenyl or alkynyl group of up to 5 carbon atoms;

$R_2$ is hydrogen, halo, alkyl of up to 5 carbon atoms, haloalkyl of up to 5 carbon atoms, $R_5$—Y— in which Y and $R_5$ are as defined above, nitro, $R_6$O-CO— or $R_7R_8$NCO—, in which $R_6$ is an alkyl, alkenyl, or alkynyl group of up to 5 carbon atoms; and each of $R_7$ and $R_8$ are hydrogen or an alkyl, alkenyl or alkynyl group of up to 5 carbon atoms;

$R_3$ is hydrogen, halo, alkyl of up to 4 carbon atoms, alkoxy of up to 4 carbon atoms, alkylthio of up to 4 carbon atoms, haloalkyl of up to 4 carbon atoms, haloalkoxy of up to 4 carbon atoms or alkoxyalkyl of up to 4 carbon atoms; and $R_4$ is halogenated alkoxy or halogenated alkylthio of up to 4 carbon atoms.

* * * * *